United States Patent [19]

Platzek et al.

[11] Patent Number: 5,410,043
[45] Date of Patent: Apr. 25, 1995

[54] PROCESS FOR THE PRODUCTION OF MONO-N-SUBSTITUTED TETRAAZA MACROCYCLES

[75] Inventors: Johannes Platzek; Heinz Gries, both of Berlin, Germany

[73] Assignee: Schering Aktiengesellschaft, Berlin and Bergkamen, Germany

[21] Appl. No.: 141,445

[22] Filed: Oct. 25, 1993

Related U.S. Application Data

[63] Continuation of Ser. No. 986,058, Dec. 7, 1992, abandoned.

[30] Foreign Application Priority Data

Dec. 6, 1991 [DE] Germany .................. 41 40 779.2
Nov. 6, 1992 [DE] Germany .................. 42 37 943.1

[51] Int. Cl.$^6$ ............... C07D 295/18; C07F 9/6524; A61K 31/28
[52] U.S. Cl. ................... 540/465; 540/474; 424/4; 424/9
[58] Field of Search ................... 540/474, 465

[56] References Cited

U.S. PATENT DOCUMENTS

| | | | |
|---|---|---|---|
| 4,085,106 | 4/1978 | Atkins | 540/474 |
| 4,130,715 | 12/1978 | Atkins | 540/474 |
| 4,937,333 | 6/1990 | Garlich et al. | 540/474 |
| 4,994,560 | 2/1991 | Kruper, Jr. et al. | 540/474 |
| 5,006,643 | 4/1991 | Fazio et al. | 540/474 |
| 5,047,527 | 9/1991 | Handel et al. | 540/474 |
| 5,053,503 | 10/1991 | Dean et al. | 540/474 |
| 5,064,802 | 11/1991 | Stevens et al. | 540/474 |
| 5,064,956 | 11/1991 | Kruper, Jr. | 540/474 |
| 5,277,895 | 1/1994 | Platzek et al. | 540/465 |

FOREIGN PATENT DOCUMENTS

| | | | |
|---|---|---|---|
| 0296522 | 12/1988 | European Pat. Off. | 540/474 |
| 0353450 | 2/1990 | European Pat. Off. | 540/474 |
| 0367223 | 5/1990 | European Pat. Off. | 540/474 |
| 0374929 | 6/1990 | European Pat. Off. | 540/474 |
| 0374947 | 6/1990 | European Pat. Off. | 540/474 |
| 0389359 | 9/1990 | European Pat. Off. | 540/474 |
| 0411941 | 2/1991 | European Pat. Off. | 540/474 |
| 0434345 | 6/1991 | European Pat. Off. | 540/474 |
| 0462787 | 12/1991 | European Pat. Off. | 540/474 |
| 0468634 | 1/1992 | European Pat. Off. | 540/474 |
| 89/12631 | 12/1989 | WIPO | 540/474 |
| 92/04336 | 3/1992 | WIPO | 540/474 |

*Primary Examiner*—Robert T. Bond
*Attorney, Agent, or Firm*—Millen, White, Zelano & Branigan

[57] ABSTRACT

A new process for the production of mono-N-substituted tetraaza macrocycles, N-substituted-tri-N-carboxyalkyl tetraaza macrocycles, and/or metal complexes thereof is described.

20 Claims, No Drawings

PROCESS FOR THE PRODUCTION OF MONO-N-SUBSTITUTED TETRAAZA MACROCYCLES

This application is a continuation of application Ser. No. 07/986,058, filed Dec. 7, 1992, now abandoned.

The invention relates to a process for the production of mono-N-substituted tetraazacyclododecane and tetraazacyclotetradecane derivatives, as well as tri-N-carboxyalkyl tetraaza macrocycles and metal complexes of tri-N-carboxyalkyl tetraaza macrocycles therefrom.

BACKGROUND OF THE INVENTION

Mono-N-substituted tetraaza macrocycles of general formula I

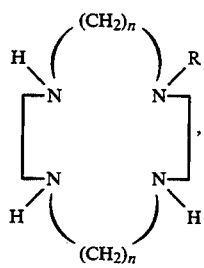

in which
n stands for the numbers 2 or 3,
R stands for a β-carboxylalkyl or β-carboxylate alkyl, β-cyanide alkyl, β-carboxamidoalkyl, β-hydroxyalkyl, aminocarbonyl, aminothiocarbonyl, β-sulfamoylalkyl radical or for a second tetraazacyclododecane or tetraazacyclotetradecane molecule bound by a bis(β-hydroxy)-alkylene chain, and carboxyl and hydroxy groups are present optionally in protected form, are important precursors of tri-N-carboxyalkyl, preferably tri-N-carboxymethyl, substituted tetraaza macrocycles, which are used as diagnostic agents and therapeutic agents in the form of their complexes with metal ions of atomic numbers 21 to 29, 31, 32, 38, 39, 42–44, 49 or 57–83 (see European patent application publication no. 255471).

Because of their importance as key compounds for these complexes, above all for the preferred NMR diagnostic agents (Macrocyclic Chemistry Congress, Hamburg 1988), production of mono-N-substituted tetraaza macrocycles has been attempted in different ways, but without a satisfactory method of synthesis previously having been found.

For example, a statistical monoalkylation or monoacylation of unsubstituted tetraaza macrocycles has been described, which, however, is not suitable at least for the production of sizable amounts of substance because of the great excess of relatively costly initial amine to be used, partially very expensive chromatographic separation of the product from the initial material as well as in most cases quite moderate yields. [see Kaden, Helv. Chim. (Swiss Chem.) Acta 69, 2081 (1986); Kimura, J. Chem. Soc. Chem. Commun. 1158 (1986); Kaden, Top. Curr. Chem. 121, 157 (1984); European patent applications no. 296522 and no. 3553450].

If it is desired—in contrast to the above-described statistical monosubstitution—to perform a specific monosubstitution, two variants are possible:

a) reaction of a tetraaza macrocycle, provided with three nitrogen protecting groups, which was obtained by statistical trisubstitution, b) reaction of a tetraaza macrocycle, provided with three nitrogen protecting groups, which was produced by specific synthesis.

In the first-mentioned variant, the precursor carrying the protecting groups (e.g., tosylate, benzoate) on three nitrogen atoms is produced by statistical trisubstitution of an unsubstituted tetraaza macrocycle, so that the above-mentioned drawbacks of a statistical reaction, such as low yields, separating problems (particularly, in the production of sizable amounts of substance) also occur here [see, e.g., Macrocyclic Chemistry Congress, Hamburg 1988]. After the subsequent specific monosubstitution to introduce substituent R [Ciampolini, J. Chem. Soc. Chem. Commun. 998 (1984): Kaden, Helv. Chim. Acta 66, 861 (1983); Basefield, Inorg. Chem. 25, 4663 (1986)], the protecting groups on the three nitrogen atoms have to be removed, e.g., by alkali metal in ammonia [Helv. Chim. Acta, 56, 2216 (1973); Helv. Chim. Acta 59, 1566 (1976); J. Org. Chem. 53, 3521 (1988)], lithium aluminum hydride [F. Voegtle; Liebigs Ann. Chem. (1977), 1344], Red-A ® [E. H. Gold, J. Org. Chem. (1972), 37, 2208], Na-Hg [M. Kellog, J. Org. Chem. 1984, 49, 110], electrolysis [M. Hesse, Helv. Chim. Acta 71 (1988), 7, 1708] or hydrobromic acid/phenol/glacial acetic acid [N. G. Lukyanenko, Synthesis, 1988, 355]. These processes of the cleavage of the protecting groups are generally connected with poor yields, limit the batch size with respect to the amount of reagent to be used (e.g., in the Na-Hg method) and above all cannot be used in the case of substituents, which carry sensitive groups (e.g., hydroxyalkyl).

If the procedure is performed according to variant b), i.e., if it is desired to produce the tetraaza macrocycle precursor carrying protecting groups on three nitrogen atoms by specific synthesis, a start is made from two reactants, which are cyclized according to methods known in the literature [e.g., Richman, Org. Synthesis 58, 86 (1978); Atkins, J. Amer. Chem. Soc. 96, 2268 (1974)]; one of the two reactants contains a protected nitrogen atom and carries, on the chain end, two volatile groups (e.g., bromine, mesyloxy, tosyloxy, triflate or alkoxycarbonyl groups), which are nucleophilically displaced from the terminal nitrogen atoms of the second reactant, of a—unlike the first reactant—protected triaza compound.

(If a reactant with two terminal ester groups is used, the two amide groupings resulting by the cyclization—preferably with diborane in THF—have to be reduced. But especially this cyclization variant is unsuitable for the production of substantial amounts of substance, since this reaction is to be performed in the highest possible dilution, to avoid, e.g., polymerization reactions: see Tabushi, Tetrahed. Lett. 12, 1049 (1977); Kaden, Inorg. Chem. 25, 321 (1986). Also, the working up of the subsequent diborane reduction—again above all in greater batches—is not without problems.)

After cleavage of one protecting group, the thus released imino grouping can be alkylated or acylated. As an example, there can be mentioned the reaction of the disodium salt of N,N',N''-tris-(p-tolylsulfonyl)-diethylene triamine [Ciampolini, J. Chem. Soc. Chem. Commun. 998 (1984)] with N-bis-(2-methanesulfonyloxy-ethyl)-triphenylmethylamine in dimethylformamide at 80°-150° C. with subsequent cleavage of the trityl group under acid conditions. The yields of both reaction steps are generally poor. Also, this variant b) is affected with the drawbacks mentioned under a) regarding the cleavage of three protecting groups coming from the second reactant.

Besides the previously presented process of the statistical and specific monosubstitution, a specific ring synthesis, in which desired substituent R already is contained in one of the two reactants to be used in the cyclization reaction, is also possible.

Besides the problems, already described above, of the cleavage of the protecting groups, it has turned out that the thus performed cyclizations generally take place with smaller yields—as compared to the reactions of the reactant provided only with protecting groups—[see Atkins, J. Amer. Chem. Soc. 96, 2268 (1974); Richman, Org. Synthesis 58, 86 (1978); Fabbrizzi, Inorg. Chem. 25, 4131 (1986); Gazetta, Chimica Italiana 115, 399 (1985)]. Further, the reactants carrying substituent R first have to be specially synthesized in a reaction sequence often comprising several steps [see, e.g., Bulkowski, J. Org. Chem. 47, 412 (1982)].

Despite varied efforts, it therefore previously has not been possible to find a satisfactory method of synthesis for mono-N-substituted tetraaza macrocycles of general formula I, which are to be considered as key compounds for the tri-N-carboxyalkyl metal complexes being used as valuable NMR and X-ray contrast media.

SUMMARY OF THE INVENTION

An object of the invention, therefore, is to make available a process for production of mono-N-substituted tetraaza macrocycles, which is suitable above all for the production of substantial amounts of substance. A further object is to provide a process for production of N-substituted-tri-N-carboxyalkyl tetraaza macrocycles and metal complexes thereof.

Upon further study of the specification and appended claims, further objects and advantages of this invention will become apparent to those skilled in the art.

These objects are achieved by the present invention.

It has been determined, surprisingly, that a selective monofunctionalization of mono-N-substituted tetraaza macrocycles of general formula I

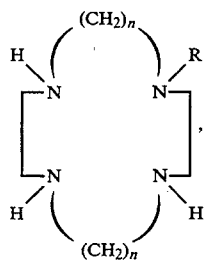  (I)

in which n stands for the number 2 or 3,

R stands for a β-carboxylalkyl or β-carboxylate alkyl, β-cyanide alkyl, β-carboxamidoalkyl, β-hydroxyalkyl, aminocarbonyl, aminothiocarbonyl, β-sulfamoylalkyl radical or for a second tetraazacyclododecane or tetraazacyclotetradecane molecule bound by a bis(β-hydroxy)-alkylene chain, and wherein carboxyl and hydroxy groups are present optionally in protected form, is achieved, if tetraazatricyclotridecane or tetraazatricyclopentadecane of general formula II

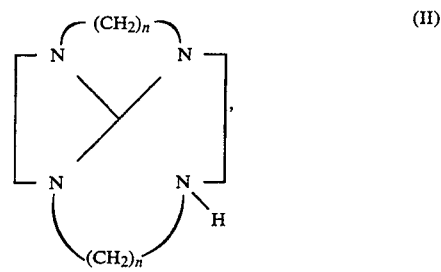  (II)

is reacted with an α,β-unsaturated ester, amide or nitrile, or an epoxide, isocyanate, isothiocyanate, aziridine or a bisepoxide, with or without solvent at about 0° to 220° C., preferably room temperature to 210° C., within about 1 to 48 hours, preferably 5 to 12 hours, optionally at a pressure up to about 100 atm. The thus obtained reaction mixture after cooling to about −20° C. to 80° C., preferably 0° C. to 30° C., is mixed with a mixture of water/organic solvent and stirred for about 0.5 to 12 hours, preferably 0.5 to 3 hours at about −20° C. to room temperature (e.g., about 25° C.), preferably 0° C. to room temperature. The thus formed—optionally to be isolated—intermediate products carrying a formyl group on a nitrogen atom are reacted by adding an inorganic base or an acid at about 0° to 150° C., preferably room temperature to 120° C., within about 1 to 72, preferably 6 to 24 hours, with stirring—optionally followed by subsequent removal of protecting groups in a way usual in the art—to obtain the end product of formula I, which can then be isolated in a way known in the art, preferably as hydrochloride.

The tetraazatricyclotridecane or tetraazatricyclopentadecane of general formula II used as intermediates are accessible according to methods known in the literature, e.g., by reacting 1,4,7,10-tetraazacyclododecane or 1,4,8,11-tetraazacyclotetradecane with dimethylformamidedimethylacetal (U.S. Pat. Nos. 4,085,106 and 4,130,715), J. Am. Chem. Soc. 102, 6364 (1980), EP 292 689.

Advantageously, this reaction step is included in the process according to the invention, without the intermediates of general formula II having to be isolated ("one-pot reaction").

A special embodiment of the process according to the invention is the production of compounds of general formula I with R meaning a

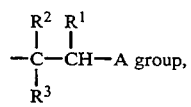

in which $R^1$ stands for a hydrogen atom, a straight-chain or cyclic $C_1$-$C_6$ alkyl, a phenyl or benzyl group—in which the phenyl or benzyl group can be substituted respectively by 1 to 2 chlorine, bromine, nitro, $C_1$-$C_7$ alkoxy, $C_7$-$C_{10}$ aralkoxy, and/or $CO_2R^4$ radicals with $R^4$ meaning a hydrogen atom, a $C_1$-$C_6$ alkyl, phenyl or benzyl group, $R^2$ and $R^3$, independent of one another each stand for $R^1$ or a $CO_2R^4$ group,
A stands for a CN, $CO_2R^4$ or

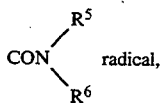

radical, in which $R^5$ and $R^6$, independent of one another, each stand for a hydrogen atom, a saturated or unsaturated, straight-chain, branched-chain or cyclic hydrocarbon radical with up to 16 C atoms, optionally interrupted by 1 to 8 oxygen atoms, or 1 to 3 phenylene or phenylenoxy groups, and optionally substituted by 1 to 5 hydroxy groups or 1 to 2 $CO_2R^4$ radicals; for phenyl or benzyl radicals optionally substituted by 1 to 3 hydroxy or $C_1$–$C_6$ alkoxy groups; or $R^5$ and $R^6$ together with the nitrogen atom stand for a saturated or unsaturated 5- or 6-ring, optionally containing another nitrogen, oxygen, sulfur atom or a carbonyl group, which optionally is substituted by 1 to 3 $C_1$–$C_6$ alkyl radicals optionally substituted by 1 to 3 hydroxy groups, and optionally present hydroxy and/or carboxyl groups optionally are protected, characterized in that tetraazatricyclotridecane or tetraazatricyclopentadecane is reacted with a feedstock of general formula III

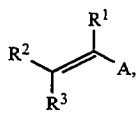

(III)

in which $R^1$, $R^2$, $R^3$ and A have the above-indicated meanings, and optionally present hydroxy and/or carboxyl groups are optionally protected, with or without solvent, preferably aprotic solvents, such as, e.g., benzene, toluene, dichloromethane, tetrahydrofuran, dioxane, acetonitrile, dimethylformamide, hexane or ether, are used as solvent, at about 0° C. to 210° C., preferably 50° C. to 180° C. (and in the case of the higher reaction temperature, the solvent used optionally to dissolve the added feedstock of general formula III was previously distilled off in a vacuum), within about 12 to 48, preferably 5 to 12 hours. The thus obtained reaction mixture is cooled to about −20° C. to 80° C., preferably 0° to 30° C., mixed with a mixture of water/organic solvent, such as, e.g., methanol, ethanol, isopropanol, tetrahydrofuran or dioxane, and stirred for about 0.5 to 12 hours, preferably 0.5 to 3 hours, at about −20° C. to room temperature, preferably 0° C. to room temperature. The thus formed—optionally to be isolated—intermediate product carrying a formyl group on a nitrogen atom is reacted by adding an inorganic base such as, e.g., lithium hydroxide, sodium hydroxide, potassium hydroxide, barium hydroxide or calcium hydroxide, preferably sodium hydroxide and potassium hydroxide, or a mineral acid, such as, e.g., hydrochloric, sulfuric or hydrobromic acid, preferably hydrochloric acid, at about 0° C. to 150° C., preferably room temperature to 120° C., within about 1 to 72 hours, preferably 6 to 24 hours, with stirring—optionally followed by subsequent removal of protecting groups in a way usual in the art—to obtain the end product of formula I, which can then be isolated in a way known in the art, preferably as hydrochloride.

If $R^1$ stands for a $C_1$–$C_6$ alkyl group, the methyl and ethyl group is preferred. Other preferred radicals for $R^1$ are the hydrogen atom and the optionally substituted phenyl radical. As preferred substituents on the phenyl ring, the nitro group, the $C_1$–$C_7$ alkoxy radical, above all the methoxy and ethoxy radical, and the $CO_2R^4$ radical, can be mentioned, with $R^4$ being preferably hydrogen, methyl, ethyl, t-butyl or benzyl.

As preferred radicals standing for $R^5$ and $R^6$, hydrogen, methyl, ethyl, 2-hydroxyethyl, 2-hydroxy-1-(hydroxymethyl)-ethyl, 1-(hydroxymethyl)-ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, 2-methoxyethyl, hexyl, decyl, tetradecyl, triethylene glycol methyl ether, tetraethylene glycol methyl ether and methoxybenzyl group can be mentioned. The amide radical can also be a heterocyclic 5- or 6-ring formed with the inclusion of the amide nitrogen. As examples, there can be mentioned: pyrrolidinyl, piperidyl, pyrazolidinyl, pyrrolinyl, pyrazolinyl, piperazinyl, morpholinyl, imidazolidinyl, oxazolidinyl, and thiazolidinyl.

In substrate III, optionally present carboxyl and/or hydroxy groups are present preferably in protected form.

As acid protecting groups, lower alkyl (e.g., $C_{1-7}$), aryl (e.g., $C_{6-10}$) and aralkyl (e.g., $C_{7-12}$) groups, for example, methyl, ethyl, propyl, n-butyl, t-butyl, phenyl, benzyl, diphenylmethyl, triphenylmethyl, bis(p-nitrophenyl)-methyl as well as trialkylsilyl (e.g., with $C_{1-4}$-alkyl groups), are suitable.

The cleavage of the protecting groups takes place according to the processes known to one skilled in the art, for example, by hydrolysis, hydrogenolysis, alkaline saponification of the esters with alkali in aqueous alcoholic solution at temperatures of 0° to 50° C., acid saponification with mineral acids or in the case of, e.g., tert-butyl esters with the help of trifluoroacetic acid.

As hydroxy protecting groups, e.g., benzyl, 4-methoxybenzyl, 4-nitrobenzyl, trityl, diphenylmethyl, trimethylsilyl, dimethyl-t-butylsilyl, and diphenyl-t-butylsilyl groups are suitable.

The hydroxy groups can also be present, e.g., as THP-ether, α-alkoxyethylether (e.g., with $C_{1-7}$-alkoxy groups), MEM-ether or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protecting groups can be released according to the methods in the literature known to one skilled in the art, e.g., by hydrogenolysis, reductive cleavage with lithium/ammonia, acid treatment of the ethers and ketals or alkali treatment of the esters (see, e.g., "Protective Groups in Organic Synthesis," T. W. Greene, John Wiley and Sons 1981).

Another special embodiment of the process according to the invention is the production of compounds of general formula I with R meaning a

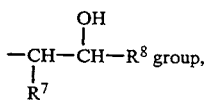 group, in which

R⁷ and R⁸, independent of one another respectively stand for a hydrogen atom, a $C_1$-$C_{20}$ alkyl radical, optionally interrupted by 1 to 10 oxygen atoms, a phenylene, phenylenoxy or phenylenedioxy group, which optionally is substituted by 1 to 3 $C_1$-$C_6$ alkyl, 1 to 3 trifluoromethyl, 1 to 7 hydroxy, 1 to 3 $C_1$-$C_7$ alkoxy, 1 to 3 $C_7$-$C_{10}$ aralkoxy, 1 to 2 $CO_2R^{4'}$ and/or 1 to 2 phenoxy or phenyl groups optionally substituted by 1 to 2 chlorine, bromine, nitro or $C_1$-$C_6$alkoxy radicals, $R^{4'}$ stands for hydrogen, $C_1$-$C_6$ alkyl, $C_6$-$C_{10}$ aryl, or $C_6$-$C_{10}$-Ar($C_1$-$C_4$) alkyl, and the optionally present hydroxy radicals are optionally in protected form, characterized in that tetraazatricyclotridecane or tetraazatricyclopentadecane is reacted with a feedstock of general formula IV

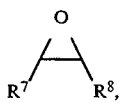 (IV)

in which $R^7$ and $R^8$ have the above-indicated meanings and wherein optionally present hydroxy and/or carboxyl groups optionally are protected, with or without solvent, preferably aprotic solvents, such as, e.g., benzene, toluene, dichloromethane, tetrahydrofuran, dioxane, acetonitrile, dimethylformamide, dimethylacetamide, dimethylsulfoxide, hexane or ether are used as solvent, at about 0° C. to 220° C., preferably 50° C. to 180° C. (and in the case of the higher reaction temperature, the solvent optionally used to dissolve the added feedstock of general formula IV was previously distilled off in a vacuum) or in an autoclave at an excess pressure of about 1 to 100 atm. within about 1 to 48 hours, preferably 5 to 12 hours. The thus obtained reaction mixture is cooled to about −20° C. to 80° C., preferably 0° C. to 30° C., mixed with a mixture of water/organic solvent, such as, e.g., methanol, ethanol, isopropanol, tetrahydrofuran or dioxane and stirred for about 0.5 to 12 hours, preferably 0.5 to 3 hours, at about −20° C. to room temperature, preferably 0° C. to room temperature. The thus formed—optionally to be isolated—intermediate product carrying a formyl group on a nitrogen atom is reacted by adding an inorganic base, such as, e.g., lithium hydroxide, sodium hydroxide, potassium hydroxide, barium hydroxide or calcium hydroxide, preferably sodium hydroxide and potassium hydroxide, or a mineral acid, such as, e.g., hydrochloric, sulfuric or hydrobromic acid, preferably hydrochloric acid, at about 0° C. to 150° C., preferably room temperature to 120° C., within about 1 to 72 hours, preferably 6 to 24 hours, with stirring—optionally followed by subsequent removal of the protecting groups in a way usual in the art—to obtain the end product of formula I, which can then be isolated in a way known in the art, preferably as hydrochloride.

Preferred radicals $R^7$ and $R^8$ are hydrogen, methyl, ethyl, hydroxymethyl, 2-hydroxyethyl, 2-hydroxy-1-(hydroxymethyl)-ethyl, 1-(hydroxymethyl)-ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, 2-methoxyethyl, hexyl, decyl, tetradecyl, triethylene glycol methyl ether, tetraethylene glycol methyl ether and methoxybenzyl as well as

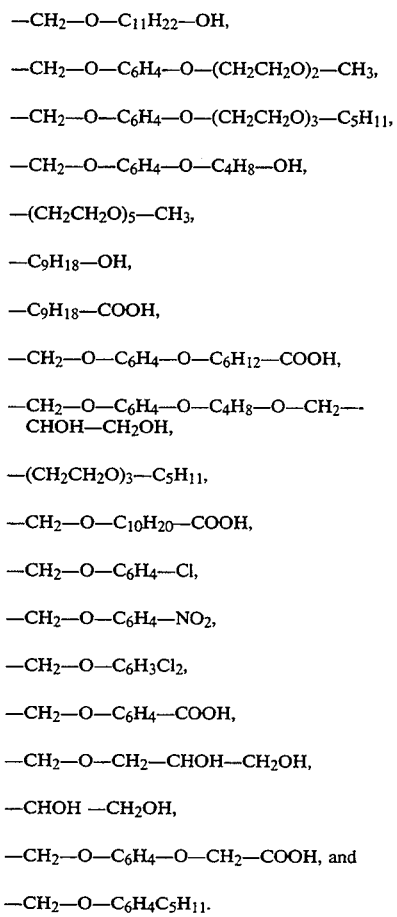

In the use of volatile epoxides, such as, e.g., ethylene oxide or propylene oxide, the reaction is performed in an autoclave.

In substrate IV, optionally present carboxyl and/or hydroxy groups are present preferably in protected form, as described above in the case of substrate III. Another special embodiment of the process according to the invention is the production of compounds of general formula I with R meaning a

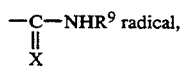 radical, in which

X means an oxygen or sulfur atom and $R^9$ means a phenyl, 1- or 2-naphthyl or straight-chain or cyclic $C_1$-$C_6$ alkyl group, characterized in that tetraazatricyclotridecane or tetraazatricyclopentadecane is reacted with a feedstock of general formula V $$R^9-N=C=X \quad (V),$$

in which X and $R^9$ have the above-indicated meaning, with or without solvent, preferably aprotic solvents, such as, e.g., benzene, toluene, dichloromethane, tetrahydrofuran, dioxane, acetonitrile, dimethylformamide, hexane or ether, are used as solvent, at about 0° C. to 180° C., preferably room temperature to 150° C. (and in the case of the higher reaction temperature, the solvent used optionally to dissolve the added feedstock of general formula V was distilled off previously in a vacuum), within about 1 to 48 hours, preferably 5 to 12 hours. The thus obtained reaction mixture is cooled to about −20° C. to 80° C., preferably 0° C. to 30° C., mixed with a mixture of water/organic solvent, such as, e.g., methanol, ethanol, isopropanol, tetrahydrofuran or dioxane, and stirred for about 0.5 to 12 hours, preferably 0.5 to 3 hours, at about −20° C. to room temperature, preferably 0° C. to room temperature. The thus formed—optionally to be isolated—intermediate product carrying a formyl group on a nitrogen atom is reacted by adding an inorganic base such as, e.g., lithium hydroxide, sodium hydroxide, potassium hydroxide, barium hydroxide or calcium hydroxide, preferably sodium hydroxide and potassium hydroxide, or a mineral acid, such as, e.g., hydrochloric, sulfuric or hydrobromic acid, preferably hydrochloric acid, at about 0° C. to 150° C., preferably room temperature to 120° C., within about 1 to 72 hours, preferably 6 to 24 hours, with stirring to obtain the end product of formula I, which can then be isolated in a way known in the art, preferably as hydrochloride.

Still another special embodiment of the process according to the invention is the production of compounds of general formula I with R meaning a —(CH$_2$)$_2$—NH—SO$_2$—R$^{10}$ radical, in which R$^{10}$ means a C$_1$-C$_6$ alkyl, —CF$_3$ or a phenyl group optionally substituted by a C$_1$-C$_6$ alkyl, chlorine, bromine or nitro radical,
characterized in that tetraazatricyclotridecane or tetraazatricyclopentadecane is reacted with a feedstock of general formula VI

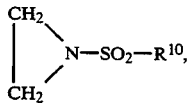

in which R$^{10}$ has the above-indicated meaning, with solvent, preferably aprotic solvents, such as, e.g., benzene, toluene, dichloromethane, tetrahydrofuran, dioxane, acetonitrile, dimethylformamide, hexane or ether, are used as solvent, at about 0° C. to 180° C., preferably room temperature to 150° C. (and in the case of the higher reaction temperature, the solvent used was distilled off previously in a vacuum), within about 1 to 48 hours, preferably 5 to 12 hours. The thus obtained reaction mixture is cooled to about −20° C. to 80° C., preferably 0° C. to 30° C., mixed with a mixture of water-/organic solvent, such as, e.g., methanol, ethanol, isopropanol, tetrahydrofuran or dioxane, and stirred for about 0.5 to 12 hours, preferably 0.5 to 3 hours, at about −20° C. to room temperature, preferably 0° C. to room temperature. The thus formed—optionally to be isolate-d—intermediate product carrying a formyl group on a nitrogen atom is reacted by adding an inorganic base such as, e.g., lithium hydroxide, sodium hydroxide, potassium hydroxide, barium hydroxide or calcium hydroxide, preferably sodium hydroxide and potassium hydroxide, or a mineral acid, such as, e.g., hydrochloric, sulfuric or hydrobromic acid, preferably hydrochloric acid, at about 0° C. to 150° C., preferably room temperature to 120° C., within 1 to 72 hours, preferably 6 to 24 hours, with stirring to the end product of formula I, which can then be isolated in a way known in the art, preferably as hydrochloride.

Preferred radicals R$^{10}$ are the phenyl radical and 4-methylphenyl radical.

Another special embodiment of the process according to the invention is the production of dimers, i.e., compounds of general formula I with R meaning a second 1,4,7,10-tetraazacyclododecane or 1,4,7,10-tetraazacyclotetradecane molecule bound by a

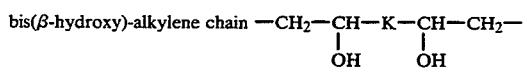

in which K means a C$_0$-C$_{16}$ alkylene chain optionally substituted by 1 to 6 hydroxy, 1 to 6 C$_1$-C$_7$ hydroxyalkyl, 1 to 8 C$_1$-C$_7$ alkoxy, 1 to 8 C$_7$-C$_{10}$ aralkoxy, and/or 1 to 2 benzyloxy groups, and optionally interrupted by 1 to 6 oxygen atoms, 1 to 2 phenylene, phenylenoxy or phenylenedioxy groups, and the optionally present hydroxy groups optionally are present in protected form, characterized in that tetraazatricyclotridecane or tetraazatricyclopentadecane is reacted with a feedstock of general formula VII

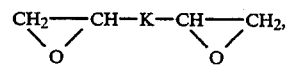 (VII)

in which K has the above-indicated meaning, and optionally present hydroxy groups are optionally protected, with or without solvent, preferably aprotic solvents, such as, e.g., benzene, toluene, dichloromethane, tetrahydrofuran, dioxane, acetonitrile, dimethylformamide, hexane or ether, are used as solvent, at about 0° C. to 220° C., preferably 50° C. to 180° C. (and in the case of the higher reaction temperature, the solvent used optionally to dissolve the added feedstock of general formula VII was distilled off previously in a vacuum) or in an autoclave at an excess pressure of about 1 to 100 atm. within about 1 to 48, preferably 5 to 12 hours. The thus obtained reaction mixture is cooled to about −20° C. to 80° C., preferably 0° to 30° C., mixed with a mixture of water/organic solvent, such as, e.g., methanol, ethanol, isopropanol, tetrahydrofuran or dioxane, and stirred for about 0.5 to 12 hours, preferably 0.5 to 3 hours, at about −20° C. to room temperature, preferably 0° C. to room temperature. The thus formed—optionally to be isolated—intermediate product carrying a formyl group on a nitrogen atom is reacted by adding an inorganic base such as, e.g., lithium hydroxide, sodium hydroxide, potassium hydroxide, barium hydroxide or calcium hydroxide, preferably sodium hydroxide and potassium hydroxide, or a mineral acid, such as, e.g., hydrochloric, sulfuric or hydrobromic acid, preferably hydrochloric acid, at about 0° C. to 150° C., preferably room temperature to 120° C., within about 1 to 72 hours, preferably 6 to 24 hours, with stirring—optionally followed by subsequent removal of protecting groups in a way usual in the art—to obtain the end product of formula I, which can then be isolated in a way known in the art, preferably as hydrochloride.

Preferred binding links K are, for example,

—C$_2$H$_4$—

—CH$_2$—

—CH$_2$—O—CH$_2$—

—CH$_2$—O—CH$_2$—CH$_2$—O—CH$_2$—

—CH$_2$—O—(CH$_2$CH$_2$O)$_2$—CH$_2$—

—CHOH—

—CHOH—CHOH—

—CHOH—CHOH—CHOH—

—CH$_2$—O—CH$_2$—CHOH—CH$_2$—O—CH$_2$—

—CH$_2$—O—C$_6$H$_4$—O—CH$_2$—

—CH$_2$—O—C$_4$H$_8$—O—CH$_2$—

—C(CH$_2$OH)$_2$—

—CH(CH$_2$OH)—

—CH$_2$—O—C$_6$H$_4$—O—C$_6$H$_4$—O—CH$_2$—

—CHOH—CHOH—CHOH—CHOH—

—CH$_2$—O—CH$_2$—CH(CH$_2$OH)$_2$—CH$_2$—O—CH$_2$—

—CH$_2$—CH(CH$_2$OCH$_3$)—CH$_2$—

—CH(OCH$_3$)—

—CH$_2$—O—CH$_2$—C$_6$H$_4$—CH$_2$—O—CH$_2$—

In contrast to substrates III to VI, which—as compared with feedstock II—are reacted equimolarly to any excess, preferably with 1.05 to 2.0 equivalents, substrate VII is used in a deficiency of 0.5 to 0.3 equivalents.

In substrate VII, optionally present hydroxy groups are present preferably in protected form, as described above in the case of substrate III.

The above-described process according to the invention is distinguished by high yields, a small number of reaction steps, great variation range in desired substituents R, problem-free performance of large batches (upscaling), partially by possible dispensing with solvent, as well as problem-free purification of the end products.

In accordance with a further embodiment, the invention relates to a process for production of N-substituted-tri-N-carboxyalkyl (e.g., C$_1$-C$_6$-alkyl)-1,4,7,10-tetraazacyclododecane and N-substituted-tri-N-carboxyalkyl (e.g., C$_1$-C$_6$-alkyl)-1,4,8,11-tetraazacyclotetradecane derivatives and metal complexes thereof, in particular, N-$\beta$-hydroxyalkyl-tri-N-carboxyalkyl-1,4,7,10-tetraazacyclododecane and N-$\beta$-hydroxyalkyl-tri-N-carboxyalkyl-1,4,8,11-tetraazacyclotetradecane derivatives and metal complexes thereof.

In German laid-open specification DE 36 25 417 A1, there is described a process for production of metal complexes of N-substituted-tri-N-carboxyalkyl-1,4,7,10-tetraazacyclododecane, wherein tri-N-ethoxycarbonylmethyl-1,4,7,10-tetraazacyclododecane derivatives, having a substituent on the fourth nitrogen atom, are converted, after cleavage of the still present carboxy protective groups, into metal complexes. The cyclic initial material needed for this process is obtained by specific ring synthesis. Thus, the process begins from two reactants, which are cyclized according to methods known from the literature [e.g., Richman, Org. Synthesis 58, 86 (1978); Atkins, J. Amer. Chem. Soc. 96, 2268 (1974)]. One of the two reactants contains a protected nitrogen atom and carries on the chain end two leaving groups (e.g., bromine, mesyloxy, tosyloxy, triflate or alkoxycarbonyl groups) which are nucleophilically displaced from the terminal nitrogen atoms of the second reactant which is a—unlike the first reactant—protected triaza compound.

The protective group chemistry used in the process of DE 36 25 417 A1 always leads to additional reaction steps in which the protective group must be removed. Further, large amounts of salts accumulate in the cleavage process which must be disposed of. Therefore, an avoidance of protective groups, especially for an industrial scale process, is desirable.

Tweedle et al. describe in European patent application 292 689 A7 and in publication Inorg. Chem. 1991, 30, 1265–1269 that starting from the unsubstituted macrocyclic compound 1,4,7,10-tetraazacyclododecane, the N-formyl compound can be obtained by a tricyclic intermediate stage. This compound still carrying three unprotected nitrogen atoms is trialkylated, deformylated and converted to the tetrasubstituted tetraaza macrocycle with haloacetic ester derivatives. After cleavage of the carboxy protective groups, the tetrasubstituted complexing agent is obtained which can be reacted to form the metal complex.

The synthesis method for metal complexes described by Tweedle et al. for N-substituted-tri-N-carboxyalkyl-1,4,7,10-tetraazacyclododecane derivatives has not only the disadvantage of an unsatisfactorily high number of steps but it is not very suitable because of the high expenses for purification of the intermediate steps and high costs for large amounts of ion exchangers necessary for the production on an industrial scale. Further, although a reaction of tri-N-carboxymethyl-1,4,7,10-tetraazacyclododecane (DO3A, compound (2) in Inorg. Chem. Vol. 30, No. 6, 1991, 1267) with primary epoxides is possible, the yields for the reaction with secondary epoxides are, however, clearly inferior and poorly suitable for use on an industrial scale.

Therefore, it continues to be a need for a process for the production of metal complexes of N-substituted (especially N-$\beta$-hydroxyalkyl)-tri-N-carboxyalkyl-1,4,7,10-tetraazacyclododecane and N-substituted (especially N-$\beta$-hydroxyalkyl)-tri-N-carboxyalkyl-1,4,8,11-tetraazacyclotetradecane derivatives, that as much as possible does not restrict selection of the electrophiles for use in the process and, above all, is suitable for the reaction of sizable amounts of substance.

Such a process is achieved by this embodiment of the invention, which is described in more detail below using the preferred embodiment N-$\beta$-hydroxyalkyl compounds as an example.

Production of metal complexes of N-$\beta$-hydroxyalkyl-tri-N-carboxyalkyl-1,4,7,10-tetraazacyclododecane and N-$\beta$-hydroxyalkyl-tri-N-carboxyalkyl-1,4,8,11-tetraazacyclotetradecane derivatives of general formula VIII

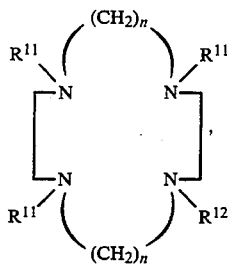
(VIII)

wherein
$R^{11}$ is $-CH_2-COOY$,
Y is hydrogen or a metal ion equivalent of an element of atomic numbers 21-32, 37-39, 42-51 or 57-83 provided that at least two substituents Y stand for metal equivalents,
n is 2 or 3,
$R^{12}$ is a

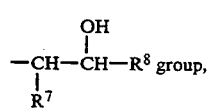
group, $R^7$ and $R^8$, independent of one another, are each hydrogen, $C_1-C_{20}$ alkyl optionally interrupted by 1 to 10 oxygen atoms, a phenylene, phenylenoxy or phenylenedioxy group, which optionally is substituted by 1 to 3 $C_1-C_6$ alkyl, 1 to 3 trifluoromethyl, 1 to 7 hydroxy, 1 to 3 $C_1-C_7$ alkoxy, 1 to 3 $C_7-C_{10}$ aralkoxy, 1 to 2 $CO_2R^{4'}$, and/or 1 to 2 phenoxy or phenyl groups optionally substituted by 1 to 2 chloro, bromo, nitro or $C_1-C_6$ alkoxy radicals,
$R^{4'}$ is hydrogen, $C_1-C_6$ alkyl, $C_6-C_{10}$ aryl or $C_6-C_{10}$-Ar($C_1-C_4$)alkyl, and
the optionally present hydroxy radicals optionally are present in protected form,
is achieved by reacting a compound of formula II, obtained from 1,4,7,10-tetraazacyclododecane or 1,4,8,11-tetraazacyclotetradecane,

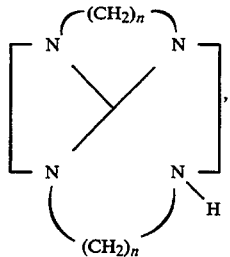
(II)

wherein n is 2 or 3, with an epoxide of general formula IV

(IV)

in which
$R^7$ and $R^8$ have the above-indicated meanings, and wherein optionally present hydroxy or carboxy groups are optionally protected, to form an intermediate of general formula IX

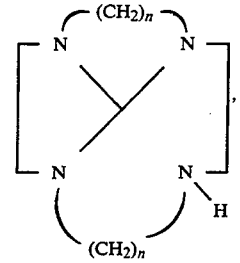
(II)

in which
$R^{12}$ has the above-indicated meaning, and optionally present hydroxy groups and/or carboxy groups are optionally protected,
the latter is saponified to form an intermediate of formula I'

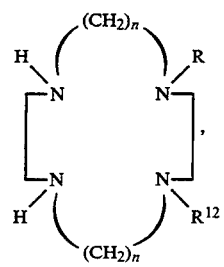
(I')

and the intermediate of formula I' is reacted in the presence of a base with a compound of formula X,

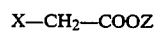
(X), in which
X is a leaving group, and
Z is hydrogen, a carboxy protective group or a metal cation,
optionally after protection of hydroxy or carboxy groups, in a polar solvent at about $-10°$ C. to 170° C. within about 1–100 hours, the protecting groups are then optionally cleaved off,
the thus obtained complexing agent of formula XI,

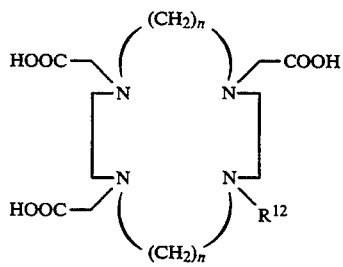
(XI)

is reacted with a metal oxide or metal salt of an element of atomic numbers 21-32, 37-39, 42-51 or 57-83 and optionally still present hydrogen atoms are also substituted by cations of inorganic and/or organic bases, amino acids or amino acid amides or the still present acid groups are converted completely or partially into esters or amides.

This embodiment of the invention exhibits the following surprising effects:

1) The desired metal complexes of general formula (VIII) are obtained in a "one-pot reaction" under favorable operating conditions in higher yields than in prior art processes;

2) The intermediates are obtained in a so surprising high purity that their isolation and purification can be dispensed with;

3) In contrast with the Tweedle et al. process, good yields are obtained even with secondary epoxides;

4) In comparison with the prior art, this embodiment according to the invention comprises fewer steps;

5) While use of protective groups is indeed possible, they are not necessary for the process according to the invention.

According to a further preferred embodiment of the invention, a compound of formula VIII is obtained

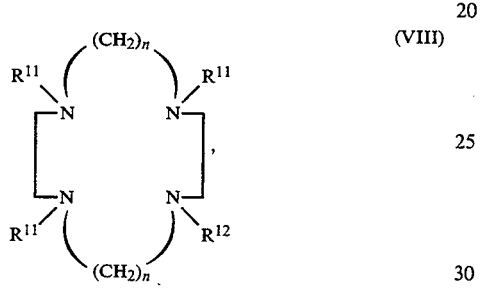

(VIII)

in which $R^{11}$ is —$CH_2$—COOY,

Y is hydrogen or a metal ion equivalent of an element of atomic numbers 21–32, 37–39, 42–51 or 57–83 provided that at least two substituents Y stand for metal equivalents, n is 2, $R^2$ is a

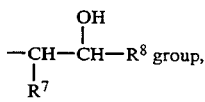

group, $R^7$ and $R^8$, independent of one another, are each hydrogen $C_1$-$C_{10}$ alkyl optionally interrupted by 1 to 5 oxygen atoms, a phenylene, phenylenoxy or phenylenedioxy group, and which is optionally substituted by 1 to 3 $C_1$-$C_6$ alkyl, 1 to 3 trifluoromethyl, 1 to 5 hydroxy, 1 to 3 $C_1$-$C_7$ alkoxy, 1 to 2 $CO_2R^{4'}$ radicals, and/or 1 to 2 phenoxy or phenyl groups optionally substituted by a nitro group or a $C_1$-$C_6$ alkoxy radical, and $R^{4'}$ is hydrogen, $C_1$-$C_6$ alkyl or benzyl.

Especially preferred is a process for the production of metal complexes of 10-(1-hydroxymethyl-2,3-dihydroxypropyl)-1,4,7-tris(carboxymethyl)-1,4,7,10-tetraazacyclododecane and of metal complexes of 10-(2-hydroxypropyl)-1,4,7-tris (carboxymethyl)-1,4,7,10-tetraazacyclododecane.

Particularly especially preferred is a process for the production of gadolinium or dysprosium complexes of 10-(1-hydroxymethyl-2,3-dihydroxypropyl)-1,4,7-tris(carboxymethyl)-1,4,7,10-tetraazacyclododecane and gadolinium or dysprosium complexes of 10-(2-hydroxypropyl)-1,4,7-tris(carboxymethyl)-1,4,7,10-tetraazacyclododecane.

As mentioned above, preferred radicals for $R^7$ and $R^8$ are hydrogen, methyl, ethyl, hydroxymethyl, 2-hydroxyethyl, 2-hydroxy-1-(hydroxymethyl) ethyl, 1-(hydroxymethyl)-ethyl, propyl, isopropyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-hydroxy-2-methylbutyl, 3-hydroxy-2-methylbutyl, 4-hydroxy-2methylbutyl, 2-hydroxyisobutyl, 3-hydroxyisobutyl, 2,3,4-trihydroxybutyl, 1,2,4-trihydroxybutyl, pentyl, cyclopentyl, 2-methoxyethyl, hexyl, decyl, tetradecyl, triethylene glycol methyl ether, tetraethylene glycol methyl ether and methoxybenzyl as well as

—$CH_2$—O—$C_{11}H_{22}$—OH,

—$CH_2$—O—$C_6H_4$—O—$(CH_2CH_2O)_2$—$CH_3$,

—$CH_2$—O—$C_6H_4$—O—$(CH_2CH_2O)_3$—$C_5H_{11}$,

—$CH_2$—O—$C_6H_4$—O—$C_4H_8$—OH, $(CH_2CH_2O)_5$—$CH_3$,

—$C_9H_{18}$—COOH,

—$C_9H_{18}$—OH,

—$CH_2$—O—$C_6H_4$—O—$C_6H_{12}$—COOH,

—$CH_2$—O—$C_6H_4$—O—$C_4H_8$—O—$CH_2$—CHOH—$CH_2OH$,

—$(CH_2CH_2O)_3$—$C_5H_{11}$,

—$CH_2$—O—$C_{10}H_{20}$—COOH,

—$CH_2$—O—$C_6H_4$—Cl,

—$CH_2$—O—$C_6H_4$—$NO_2$,

—$CH_2$—O—$C_6H_3Cl_2$,

—$CH_2$—O—$C_6H_4$—COOH,

—$CH_2$—O—$CH_2$—CHOH—$CH_2OH$,

—CHOH—$CH_2OH$,

—$CH_2$—O—$C_6H_4$—O—$CH_2$—COOH, and

—$CH_2$—O—$C_6H_4$—$C_5C_{11}$.

Alkoxy substituents in $R^7$ and $R^8$ include straight chain or branched radicals with 1 to 6 or 1 to 7 C atoms such as, for example, methoxy, ethoxy, propoxy, isopropoxy.

Alkyl groups $R^{4'}$ with 1–6 carbon atoms include straight chain or branched alkyl groups such as, for example, methyl, ethyl, propyl, isopropyl, butyl, isobutyl, tert.-butyl. Especially preferred are methyl, ethyl, tert.-butyl.

Preferred aryl groups and aralkyl groups for $R^{4'}$ are phenyl, naphthyl and benzyl groups.

Especially preferred radicals for $R^{4'}$ are hydrogen, methyl or benzyl.

Reaction Conditions for the Process Steps (II)+(IV)→(IX)→(I')    1

As described above, the reaction of the tricyclic intermediate of formula (II) with an epoxide of formula (IV) takes place, with or without solvent, at about 0° C. and 220° C., e.g., room temperature to 210° C., within about 1 to 48 hours, preferably 5 to 12 hours, optionally at a pressure of up to 100 atm.

The reaction mixture containing the compound of formula (IX), after cooling to about −20° C. to 80° C., preferably 0° C. to 30° C., is mixed with a mixture of water/organic solvent, and stirred for about 0.5 to 12 hours, preferably 0.5 to 3 hours, at about −20° C. to room temperature, preferably 0° C. to room temperature.

By addition of an inorganic base or an acid at about 0° C. to 150° C., preferably room temperature to 120° C., within about 1 to 72, preferably 6 to 24 hours, with stirring—optionally followed by subsequent protective group removal an intermediate of formula I' is obtained. The latter can also be isolated, if desired, as salt, preferably as hydrochloride.

As solvents for the reaction of compounds of formula II with compounds of formula IV, aprotic solvents above all are suitable, such as, for example, benzene, toluene, dichloromethane, tetrahydrofuran, dioxane, acetonitrile, dimethylformamide, dimethylacetamide, dimethylsulfoxide, hexane or diethylether.

The solvents used in the mixture with water can be, e.g., methanol, ethanol, isopropanol, tetrahydrofuran, dioxane.

As base or acid, for example, alkali and alkaline-earth hydroxides, alkali and alkaline-earth carbonates or mineral acids such as, e.g., hydrochloric acid or sulfuric acid or methane sulfonic acid are suitable.

(I')+(X)→(XI)  2

The bases used as acid traps in the further reaction of the intermediate of formula I' with a compound of formula X can be tertiary amines (e.g., triethylamine, trimethylamine, N,N-dimethylaminopyridine, 1,5-diazabicyclo[4.3.0]-non-5-ene (DBN), 1,5-diazabicyclo[5.4.0]-undec-5-ene (DBU)), alkali or alkaline-earth carbonates, bicarbonates, or hydroxides (e.g., lithium-, sodium-, magnesium-, calcium-, barium- and potassium-, -carbonate, -hydroxide and -bicarbonate).

The reaction takes place in a polar solvent such as, for example, water, acetonitrile, dimethylformamide, dimethylsulfoxide, hexamethylphosphoric acid triamide or tetrahydrofuran as well as in alcohols with a chain length with up to 8 C atoms such as, e.g., methanol, ethanol, propanol, isopropanol, n-butanol, isobutanol, and tert.-butanol.

The reaction is performed at temperatures of about −10° C.–170° C., preferably at 0°–120° C., especially at 40°–100° C., within about 0.5-48 hours, preferably 3–24 hours.

The optionally performed introduction or cleavage of protective groups of carboxyl- or hydroxy functions is performed in accordance with methods known in the literature.

As metal cations for Z, metal cations of the elements of alkali or alkaline-earth metals are suitable.

In a preferred embodiment, the compound of formula X is chloroacetic acid.

The intermediately obtained complexing agents of formula XI can be purified in an advantageous way by ion exchangers. For this purpose, especially preferred are cation exchangers (in the H+ form) which are first washed with water and then, eluted with aqueous ammonia solution, yield the desired product. IR 120 (H+) and AMB 252c (H+) as well as Reillex ® have proven to be especially advantageous exchangers. If Reillex ® is used, the complexing agent is eluted with water or aqueous alcohols.

(XI)→(VIII)  3

The production of the metal complexes according to formula VIII takes place in a way known in the art by reacting the complexing agents of general formula XI with a metal oxide or metal salt of an element of atomic numbers 21–32, 37–39, 42–51 or 57–83 preferably in water and/or in aqueous solutions of lower alcohols (such as, e.g., methanol, ethanol or isopropanol) at temperatures of about 20° C.–110° C., preferably 80° C.–100° C. The addition of about 0.1–4 equivalents, preferably 0.5–2 equivalents, of an inorganic or organic acid, preferably acetic acid, has proved to be especially advantageous.

The thus obtained metal complex solutions can advantageously be purified by treatment on an ion exchange cascade or in a batch, consisting of an acid cation exchanger (H+ form) and basic anion exchanger (OH− form), preferably IR 120 H+, AMB 252c/IRA 67.

The final cleaning is performed by crystallization from a lower alcohol, or an alcohol-water mixture. As alcohols there can be mentioned methanol, isopropanol; however, ethanol is preferred.

The metal salts used can be, for example, nitrates, acetates, carbonates, chlorides or sulfates. The metals contained in the metal oxide or metal salt used can be an element of atomic numbers 21–32, 37–39, 42–51 or 57–83.

The following examples are used to explain the object of the invention in more detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications cited above and of corresponding German applications P 41 40 779.2 and P 42 37 943.1, are hereby incorporated by reference.

EXAMPLES

Reactions with Compounds of General Formula III

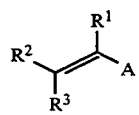

Example 1 a) Mixture of 1- and 4-formamido-10-[(2-ethoxycarbonyl)ethyl]-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is partially distilled off in this way. Then, 13.94 g (139.2 mmol) of acrylic acid ethyl ester is instilled under a nitrogen atmosphere and heated slowly (within 30 minutes) to 80° C. It is stirred for 12 hours at this temperature. It is cooled in an ice bath to 0° C., and a mixture of 150 ml of ethanol/20 ml of water is added. Then, it is stirred for 30 minutes at room temperature. It is evaporated to dryness in a vacuum and the residue is chromatographed on silica gel (mobile solvent=ethanol/-conc. aqu. ammonia=10/1). After concentration by evaporation of the main fractions, 31.71 g (91% of theory) of a yellowish oil is obtained.

Analysis (relative to the anhydrous substance): Cld: C, 55.98; H, 9.39; N, 18.65. Fnd: C, 55.91; H, 9.43; N, 18.59.

b) 10-(2-Carboxyethyl)-1,4,7,10-tetraazacyclododecane 46.32 g (825.6 mmol) of potassium hydroxide is added to 31.0 g (103.2 mmol) of the title compound of example 1a in 150 ml of ethanol/150 ml of water and refluxed for 12 hours. It is cooled in an ice bath to 0° C. It is adjusted with 6N hydrochloric acid to pH 6 and then concentrated by evaporation in a vacuum. The residue is extracted with a mixture of 300 ml of methanol/50 ml of methylene chloride and filtered off from potassium chloride. The filtrate is concentrated by evaporation in a vacuum and purified on a reversed-phase column (RP 18/mobile solvent: gradient of tetrahydrofuran/water).

Yield: 23.02 g (87% of theory) of a yellowish, viscous oil, which solidifies after a short time Analysis (relative to the anhydrous substance): Cld: C, 56.23; H, 9.44; N, 21.86. Fnd: C, 56.17; H, 9.51; N, 21.83.

Example 2

10-(2-Cyanoethyl)-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to room temperature. 9.24 g (174.15 mmol) of acrylic acid nitrile is instilled under a nitrogen atmosphere and heated slowly to 75° C. It is stirred for 9 hours at this temperature. It is cooled to room temperature and a mixture of 120 ml of methanol/30 ml of water is added. It is stirred for 10 minutes at room temperature. Then, 13.93 g (348.3 mmol) of sodium hydroxide is added and it is stirred for 24 hours at 40° C. It is evaporated to dryness in a vacuum and the residue is extracted 3 times with hot toluene (80° C.). The organic phase is dried on potassium hydroxide and concentrated by evaporation in a vacuum.

Yield: 23.28 g (89% of theory) of a pale yellow oil, which crystallizes with standing.

Analysis (relative to the anhydrous substance): Cld: C, 58.63; H, 10.29; N, 31.08. Fnd: C, 58.57; H, 10.34; N, 30.96.

Example 3

10-[(2-Phenyl-2-carboxy)-ethyl]-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to room 10 temperature. 24.55 g (139.32 mol) of 2-phenyl-vinyl acid ethyl ester is instilled under a nitrogen atmosphere and slowly heated to 130° C. It is stirred for 12 hours at this temperature. It is cooled to room temperature and a mixture of 150 ml of methanol/150 ml of water is added. Then, it is stirred for 30 minutes at room temperature. 52.11 g (928.8 mmol) of potassium hydroxide is added and refluxed for 12 hours. It is cooled in an ice bath to 0° C. and adjusted with conc. hydrochloric acid to pH 7, then evaporated to dryness. The residue is taken up in a mixture of 250 ml of methanol/50 ml of methylene chloride. The precipitated potassium chloride is filtered off and the filtrate is concentrated by evaporation in a vacuum. The residue is chromatographed on silica gel (mobile solvent=methyl-tert-butyl ether/methanol/conc. aqu. ammonia=6/2/1).

Yield: 28.27 g (76% of theory) of a vitreous solid Analysis (relative to the anhydrous substance): Cld: C, 63,72; H, 8.81; N, 17.48. Fnd: C, 63.64; H, 8.93; N, 17.37.

Example 4

11-(2-Cyanoethyl)-1,4,8,11-tetraazacyclotetradecane 13.68 g (114.8 mmol) of dimethylformamide-dimethylacetal (under nitrogen) is added to 20.0 g (99.83 mmol) of 1,4,8,11-tetraazacyclotetradecane in 200 ml of absolute toluene. It is refluxed slowly and the solvent is distilled off in this way. Then, it is concentrated by evaporation under reduced pressure. The residue is cooled to room temperature. 6.36 g (119.8 mmol) of acrylic acid nitrile is instilled under a nitrogen atmosphere and heated slowly to 75° C. It is stirred for 9 hours at this temperature. It is cooled to room temperature and a mixture of 120 ml of methanol/30 ml of water is added. It is stirred for 10 minutes at room temperature. Then, 11.98 g (299.5 mmol) of sodium hydroxide is added and it is stirred for 24 hours at 40° C. It is evaporated to dryness in a vacuum and the residue is extracted 3 times with hot toluene (80° C.). The organic phase is dried on potassium hydroxide and concentrated by evaporation in a vacuum.

Yield: 21.75 g (86% of theory) of a pale yellow oil, which crystallizes with standing Analysis (relative to the anhydrous substance): Cld: C, 61.62; H, 10.74; N, 27.64. Fnd: C, 61.53; H, 10.84; N, 27.52.

For example, the compounds listed in the following table are produced analogously.

TABLE 1a

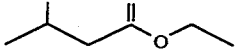

| R | Temp. (°C.) time (h) | Solvent | excess | Yield (%) | elementary analysis | |
|---|---|---|---|---|---|---|
| 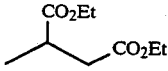 | 100° C. 12 h | — | 1,2 | 87 | C 57,30  H 9,62  N 17,82<br>C 57,35  H 9,58  N 17,87 | (cld) |
| 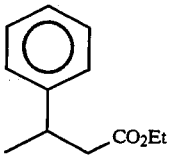 | 120° C. 12 h | — | 1,3 | 92 | C 54,82  H 8,66  N 15,04<br>C 54,73  H 8,71  N 14,97 | (cld) |
| 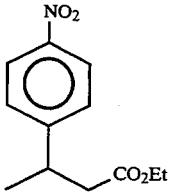 | 130° C. 12 h | — | 1,5 | 84 | C 63,80  H 8,57  N 14,88<br>C 63,75  H 8,50  N 14,84 | (cld) |
| 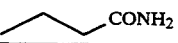 | 130° C. 12 h | $CH_2Cl_2$ | 1,5 | 81 | C 56,99  H 7,41  N 16,62<br>C 56,93  H 7,50  N 16,54 | (cld) |
| 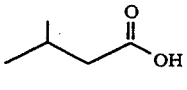 | 100° C. 24 h | — | 1,2 | 93 | C 53,11  H 9,29  N 25,81<br>C 53,20  H 9,21  N 25,74 | (cld) |

TABLE 1b

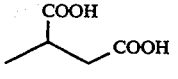

| R | base/ solvent | excess base (eq.) | Temp. (°C.) | Time (h) | Yield (%) | elementary analysis | |
|---|---|---|---|---|---|---|---|
| 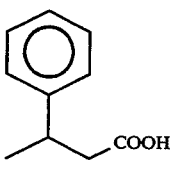 | KOH MeOH/$H_2O$ 1:1 | 8 | reflux | 12 | 83 | C 57,75  H 9,69  N 20,72<br>C 57,68  H 9,78  N 20,67 | (cld) |
| (COOH, COOH) | KOH EtOH/$H_2O$ 1:1 | 10 | reflux | 24 | 79 | C 49,99  H 8,39  N 19,43<br>C 49,90  H 8,46  N 19,37 | (cld) |
| (phenyl-COOH) | KOH MeOH/$H_2O$ 1:1 | 8 | reflux | 12 | 85 | C 63,72  H 8,81  N 17,48<br>C 63,65  H 8,87  N 17,39 | (cld) |

TABLE 1b-continued

| R | base/solvent | excess base (eq.) | Temp. (°C.) | Time (h) | Yield (%) | elementary analysis | | |
|---|---|---|---|---|---|---|---|---|
| ![NO2-phenyl-CH2-COOH] | KOH MeOH/H2O 1:1 | 8 | 50° C. | 24 | 79 | C 55,88 H 7,45 N 19,16 C 55,84 H 7,52 N 19,08 | | (cld) |
| ![CONH2] | NaOH MeOH/H2O 1:1 | 3 | RT | 24 | 89 | C 54,29 H 10,35 N 28,78 C 54,23 H 10,29 N 28,81 | | (cld) |

Reactions with Compounds of General Formula IV

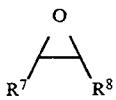

Example 5 a) Mixture of 1- and 4-formamido-10-(6-hydroxy-2,2-dimethyl-1,3-dioxepan-5-yl)-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is partially distilled off in this way. Then, 20.1 g (139.32 mmol) of 4,4-dimethyl-3,5,8-trioxabicyclo-(5.1.0)-octane is instilled under a nitrogen atmosphere and heated slowly (1 hour) to 130° C. It is stirred for 12 hours at 120° C. It is cooled to room temperature and a mixture of 120 ml of methanol/30 ml of water is added. Then, it is stirred for one hour at room temperature. It is concentrated by evaporation in a vacuum and the residue is chromatographed on silica gel (mobile solvent=methyl-tert-butyl ether/methanol/aqu. conc. ammonia=15/5/1). After concentration by evaporation of the main fractions, 36.39 g (91% of theory) of a pale yellow, viscous oil, which crystallizes with standing, is obtained.

Analysis (relative to the anhydrous substance): Cld: C, 55.79; H, 9.36; N, 16.27. Fnd: C, 55.82; H, 9.29; N, 16.20.

b) 10-(6-Hydroxy-2,2-dimethyl-1,3-dioxepan-5-yl)-1,4,7,10-tetraazacyclododecane 57.0 g (1.02 mol) of potassium hydroxide is added to 35.0 g (101.6 mmol) of the title compound of example 5a in 200 ml of methanol/50 ml of water and refluxed for 5 hours. It is evaporated to dryness in a vacuum and the residue is extracted 3 times with 200 ml of hot (80° C.) toluene. The organic phase is dried on potassium hydroxide and concentrated by evaporation in a vacuum.

Yield: 31.5 g (98% of theory) of a pale yellow, viscous oil, which becomes solid with standing Analysis (relative to the anhydrous substance): Cld: C, 56.93; H, 10.19; N, 17.71. Fnd: C, 56.87; H, 10.25; N, 17.63.

Example 6 a) Mixture of 1- and 4-formamido-10-(2-hydroxypropyl)-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to 0° C. The residue is dissolved in 50 ml of toluene and the solution is fed into an autoclave. 20.23 g (348.3 mmol) of propylene oxide is added and the autoclave is made airtight. Then, it is heated for 24 hours to 100° C. It is evaporated to dryness in a vacuum and the residue is taken up in a mixture of 120 ml of methanol/30 ml of water. Then, it is stirred for one hour at room temperature. It is concentrated by evaporation in a vacuum and the residue is chromatographed on silica gel. (Mobile solvent=methanol/isopropanol/aqu. conc. ammonia=10/5/1). After concentration by evaporation of the main fractions in a vacuum, 26.7 g (89% of theory) of a weak, yellow-colored oil is obtained.

Analysis (relative to the anhydrous substance): Cld: C, 55.79; H, 10.14; N, 21.69. Fnd: C, 55.72; H, 10.19; N, 21.61.

b) 10-(2-Hydroxypropyl)-1,4,7,10-tetraazacyclododecane 45.2 g (805.1 mmol) of potassium hydroxide is added to 26.0 g (100.63 mmol) of the title compound of example 6a in 250 ml of water and refluxed for 5 hours. It is evaporated to dryness in a vacuum and the residue is extracted 3 times with 200 ml of hot (80° C.) toluene. The organic phase is dried on potassium hydroxide and concentrated by evaporation in a vacuum.

Yield: 22.02 g (95% of theory) of a weak, yellowish oil, which solidifies after a short time Analysis (relative to the anhydrous substance): Cld: C, 57.36; H, 11.38; N, 24.32. Fnd: C, 57.30; H, 11.43; N, 24.28.

Example 7

10-[2-Hydroxy-5-(2,2-dimethyl-1,3-dioxolan-4-yl)-4-oxapentyl]-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to 40° C. 24.04 g (127 7 mmol) of 2 2-dimethyl-4-(2',3'-epoxy)propoxy-methyl-1,3-dioxolane is instilled under a nitrogen atmosphere and heated slowly (within one hour) to 110° C. It is stirred for 12 hours at this temperature. It is cooled to room temperature and a mixture of 120 ml of methanol/30 ml of $H_2O$ is added. Then, it is stirred for 30 minutes at room temperature. 65.1 g (1.16 mol) of potassium hydroxide is added and refluxed for 5 hours. Then, it is concentrated by evaporation in a vacuum and the residue is extracted 3 times with 200 ml of hot toluene (80° C.). The combined organic phases are dried on potassium hydroxide and evaporated to dryness in a vacuum. The residue is chromatographed on silica gel (mobile solvent = methanol/water/aqu. conc. ammonia = 8/2/1). The main fractions are evaporated to dryness, the residue is dissolved in 500 ml of hot toluene. It is filtered off from insolubles (silica gel) and evaporated to dryness.

Yield: 36.41 g (87% of theory) of a pale yellow, viscous oil

Analysis (relative to the anhydrous substance): Cld: C, 56.64; H, 10.07; N, 15.54. Fnd: C, 56.53; H, 10.13; N, 15.49.

Example 8

10-[3-(4-Nitrophenoxy)-2-hydroxypropyl]-1,4,7,10-tetraazacyclododecane (as tetrahydrochloride)

15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to room temperature. A solution of 29.46 g (150.93 mmol) of (4-nitrophenyl)-2,3-epoxypropyl ether in 100 ml of methylene chloride is instilled under a nitrogen atmosphere. Then, it is heated slowly to 120° C., and the methylene chloride is distilled off (toward the end under reduced pressure). It is stirred for 12 hours at 120° C. It is cooled to room temperature and a mixture of 160 ml of methanol/20 ml of water is added. Then, it is stirred for 30 minutes at room temperature. 50 ml of conc. hydrochloric acid is added and refluxed for 12 hours. Then, it is evaporated to dryness in a vacuum. The residue is recrystallized from methanol/ether.

Yield: 48.27 g (81% of theory) of a yellow-colored crystalline powder

Analysis (calculated for a Cl-free compound): Cld: C, 55.57; H, 7.95; N, 19.06. Fnd: C, 55.49; H, 8.03; N, 19.01.

Example 9 a) 11-[3-(4-Nitrophenoxy)-2-hydroxypropyl]-1,4,8,11-tetraazacyclotetradecane (as tetrahydrochloride)

13.68 g (114.8 mmol) of dimethylformamide-dimethylacetal (under nitrogen) is added to 20.0 g (99.83 mmol) of 1,4,8,11-tetraazacyclotetradecane in 200 ml of absolute toluene. It is refluxed slowly and the solvent is distilled off in this way. Then, it is concentrated by evaporation under reduced pressure. The residue is cooled to room temperature. A solution of 23.38 g (119.8 mmol) of (4-nitrophenyl)-2,3-epoxypropyl ether in 100 ml of methylene chloride is instilled under a nitrogen atmosphere. Then, it is heated slowly to 120° C., and the methylene chloride is distilled off (toward the end under reduced pressure). It is stirred for 12 hours at 120° C. It is cooled to room temperature and a mixture of 150 ml of methanol/20 ml of water is added. Then, it is stirred for 30 minutes at room temperature. 100 ml of conc. hydrochloric acid is added and refluxed for 12 hours. Then, it is evaporated to dryness in a vacuum. The residue is recrystallized from methanol/ether.

Yield: 41.61 g (77% of theory) of a yellowish, crystalline powder.

Analysis (relative to the anhydrous substance): Cld: C, 42.16; H, 6.89; N, 12.94; Cl, 26.20. Fnd: C, 42.10; H, 6.93; N, 12.90; Cl, 26.08.

Example 10 a) Mixture of 1- and 4- and 8-formamido-11-[2-hydroxy-2-(2,2-dimethyl-1,3-dioxolan-4-yl)-ethyl]-1,4,8,11-tetraazacyclotetradecane 13.68 g (114.8 mmol) of dimethylformamide-dimethylacetal (under nitrogen) is added to 20.0 g (99.83 mmol) of 1,4,8,11-tetraazacyclotetradecane in 200 ml of absolute toluene. It is refluxed slowly and the solvent is distilled off in this way. Then, it is concentrated by evaporation under reduced pressure. The residue is cooled to room temperature. 17.27 g (119.8 mmol) of 2-(2,2-dimethyl-1,3-dioxolan-4-yl)-ethylene oxide is instilled under a nitrogen atmosphere and then heated slowly to 130° C. It is stirred for 12 hours at this temperature. It is cooled to 0° C. and a mixture of 160 ml of methanol/40 ml of water is added, then it is stirred for 1 hour at room temperature. It is evaporated to dryness in a vacuum and the residue is chromatographed on silica gel (mobile solvent = methyl-tert-butyl ether/methanol/conc. aqu. ammonia = 15/5/1).

Yield: 33.1 g (89% of theory) of a pale yellow, viscous oil

Analysis (relative to the anhydrous substance): Cld: C, 58.04; H, 9.74; N, 15.04. Fnd: C, 58.13; H, 9.61; N, 14.92.

b) 11-[2-Hydroxy-2-(2,2-dimethyl-1,3-dioxolan-4-yl)ethyl]-1,4,8,11-tetraazacyclotetradecane 39.15 g (698 mmol) of potassium hydroxide is added to 32.0 g (87.22 mmol) of the title compound of example 10a in 200 ml of methanol/100 ml of water and refluxed for 5 hours. It is evaporated to dryness in a vacuum and the residue is extracted 3 times with 200 ml of hot toluene (80° C.). The organic phase is dried on potassium hydroxide and concentrated by evaporation in a vacuum.

Yield: 28.85 g (96% of theory) of a pale yellow, viscous oil, which solidifies after a short time Analysis (relative to the anhydrous substance): Cld: C, 59.27; H, 10.53; N, 16.26. Fnd: C, 59.18; H, 10.61; N, 16.17.

For example, the compounds listed in the following table are produced analogously.

TABLE 2a

Structures shown (two tautomeric forms of macrocyclic formyl-amine):

- Structure 1: 14-membered tetraazacyclic ring with CHO—N, N—R, N—R, and NH substituents
- Structure 2: same ring with H—N, N—R, N—CHO, and NH substituents

| R | Temp. (°C.) / Time (h) | Solvent | excess (epoxide) | Yield (%) | elementary analysis | | | |
|---|---|---|---|---|---|---|---|---|
| CH₃-C(CH₃)(O–)(O–CH₂)–CH(OH)–CH₂– (isopropylidene-glycerol derivative) | 130° C. / 12 h | — | 1,1 | 93 | C 55,79  H 9,36  N 16,27<br>C 55,74  H 9,29  N 16,29 | | | cld |
| PhO–CH₂–CH(OH)–CH₂– | 120° C. / 8 h | — | 1,1 | 91 | C 61,69  H 8,63  N 15,99<br>C 61,61  H 8,67  N 15,94 | | | cld |
| PhCH₂O–CH₂–CH(OH)–CH₂– | 120° C. / 8 h | — | 1,1 | 90 | C 62,61  H 8,85  N 15,37<br>C 62,64  H 8,80  N 15,41 | | | cld |
| 4-Cl-C₆H₄-O–CH₂–CH(OH)–CH₂– | 120° C. / 8 h | — | 1,1 | 92 | C 56,17  H 7,59  N 14,56  Cl 9,21<br>C 56,10  H 7,51  N 14,61  Cl 9,14 | | | cld |
| 4-CH₃O-C₆H₄-O–CH₂–CH(OH)–CH₂– | 120° C. / 8 h | CH₂Cl₂ | 1,1 | 89 | C 59,98  H 8,48  N 14,73<br>C 59,89  H 8,53  N 14,67 | | | cld |
| 4-(iPrO₂C)-C₆H₄-O–CH₂–CH(OH)–CH₂– | 130° C. / 24 h | — | 1,1 | 87 | C 62,04  H 8,68  N 12,06<br>C 62,11  H 8,60  N 11,96 | | | cld |
| iPrO–CH₂–CH(OH)–CH₂– | 120° C. / 8 h | — | 1,1 | 93 | C 56,93  H 10,19  N 17,51<br>C 55,86  H 10,25  N 17,46 | | | cld |
| CH₃–CH(OH)–CH₂–CH₂–CH₂–CH₃ (2-hexyl) | 120° C. / 8 h | — | 1,1 | 87 | C 59,97  H 10,74  N 18,65<br>C 59,92  H 10,68  N 18,71 | | | cld |
| (2-ethylhexyl)O–CH₂–CH(OH)–CH₂– | 110° C. / 12 h | — | 1,2 | 87 | C 62,14  H 10,95  N 14,49<br>C 62,03  H 10,87  N 14,36 | | | cld |
| 4-(iPrO₂C)-C₆H₄-O–CH₂–CH(OH)–CH₂– | 110° C. / 12 h | — | 1,2 | 85 | C 60,53  H 8,31  N 12,83<br>C 60,59  H 8,22  N 12,74 | | | cld |

TABLE 2b

| R | Base/solvent | excess Base (eq.) | Temp. (°C.) | Time (h) | Yield (%) | elementary analysis | | | |
|---|---|---|---|---|---|---|---|---|---|
| [CH₃CH₂-CH(OH)-CH₂-O-C(CH₃)₂-O-] (acetonide) | KOH MeOH/H₂O 4:1 | 10 | reflux | 5 | 97 | C 56,93 C 56,88 | H 10,19 H 10,25 | N 17,71 N 17,63 | (cld) |
| CH₃-CH(OH)-CH₂-O-C₆H₅ | NaOH EtOH/H₂O 5:1 | 5 | 60° C. | 24 | 97 | C 63,32 C 63,28 | H 9,38 H 9,45 | N 17,38 N 17,33 | (cld) |
| CH₃-CH(OH)-CH₂-O-CH₂-C₆H₅ | NaOH EtOH/H₂O 5:1 | 5 | 60° C. | 24 | 98 | C 64,25 C 64,14 | H 9,59 H 9,67 | N 16,65 N 16,60 | (cld) |
| CH₃-CH(OH)-CH₂-O-C₆H₄-Cl (p) | KOH EtOH/H₂O 8:1 | 5 | RT | 48 | 97 | C 57,21 C 57,14 | H 8,19 H 8,27 | N 15,70 N 15,62 Cl 9,93 Cl 9,87 | (cld) |
| CH₃-CH(OH)-CH₂-O-C₆H₄-OCH₃ (p) | KOH EtOH/H₂O 8:1 | 5 | RT | 48 | 98 | C 61,34 C 61,24 | H 9,15 H 9,08 | N 15,90 N 15,84 | (cld) |
| CH₃-CH(OH)-CH₂-O-C₆H₄-CO₂iPr (p) | NaOH Dioxan/H₂O 8:1 | 2 | RT | 48 | 92 | C 63,27 C 63,22 | H 9,23 H 9,31 | N 12,83 N 12,79 | (cld) |
| CH₃-CH(OH)-CH₂-O-CH(CH₃)₂ | NaOH MeOH/H₂O 4:1 | 10 | reflux | 5 | 98 | C 58,30 C 58,24 | H 11,18 H 11,25 | N 19,42 N 19,35 | (ber.) (cld) |
| CH₃-CH(OH)-CH₂-CH₂-CH₂-CH₃ | KOH EtOH/H₂O 4:1 | 10 | reflux | 5 | 98 | C 61,72 C 61,67 | H 11,84 H 11,91 | N 20,57 N 20,49 | (ber.) (cld) |
| CH₃-CH(OH)-CH₂-O-CH₂-CH(C₂H₅)-C₄H₉ | KOH EtOH/H₂O 4:1 | 10 | reflux | 5 | 97 | C 63,64 C 63,54 | H 11,81 H 11,90 | N 15,63 N 15,54 | (ber.) (cld) |
| CH₃-CH(OH)-CH₂-O-C₆H₄-CO₂iPr (p) | KOH EtOH/H₂O 4:1 | 3 | 30° C. | 48 | 93 | C 61,74 C 61,66 | H 8,88 H 8,95 | N 13,71 N 13,62 | (ber.) (cld) |

Reactions with Compounds of General Formula V:
$$R^9-N=C=X$$

Example 11

10-(N-Phenylcarbamoyl)-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to 0° C. 16.6 g (139.32 mmol) of phenyl isocyanate is instilled under a nitrogen atmosphere and heated slowly to 100° C. It is stirred for 12 hours at this temperature. It is cooled to room temperature and a mixture of 160 ml of ethanol/40 ml of water is added. Then, it is stirred for 10 minutes at room temperature. Then, 18.58 g (464.4 mmol) of sodium hydroxide is added and it is stirred for 24 hours at 40° C. It is evaporated to dryness in a vacuum and the residue is taken up in 400 ml of water. The aqueous phase is extracted 5 times with 200 ml of methylene chloride, the organic phase is dried on magnesium sulfate and concentrated by evaporation in a vacuum. The residue is chromatographed on silica gel (mobile solvent=methyl-tert-butyl ether/methanol/-conc. aqu. ammonia=6/3/1).

Yield: 29.1 g (86% of theory) of a pale yellow solid
Analysis (relative to the anhydrous substance): Cld: C, 61.83; H, 8.65; N, 24.03. Fnd: C, 61.71; H, 8.72; N, 23.94.

For example, the compounds listed in the following table are produced analogously.

TABLE 3a

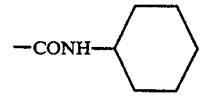

| R | Temp. (°C.) Time (h) | Solvent | excess (acyl reagent) | Yield (%) | elementary analysis | | | | |
|---|---|---|---|---|---|---|---|---|---|
| —CONH—⬡ | 100° C. 12 h | — | 1,2 | 93 | C 59,05<br>C 59,14 | H 9,60<br>H 9,53 | N 21,52<br>N 21,46 | | (cld) |
| —CONH—⬡⬡ | 100° C. 18 h | — | 1,2 | 89 | C 65,02<br>C 65,11 | H 7,37<br>H 7,30 | N 18,96<br>N 18,89 | | (cld) |
| —CSNH—⬡ | 100° C. 12 h | — | 1,1 | 90 | C 57,29<br>C 57,20 | H 7,51<br>H 7,60 | N 20,88<br>N 20,81 | S 9,56<br>S 9,59 | (cld) |
| —CSNH—⬡⬡ | 100° C. 18 h | CH$_2$Cl$_2$ | 1,1 | 87 | C 62,31<br>C 62,35 | H 7,06<br>H 7,01 | N 18,17<br>N 18,08 | S 8,32<br>S 8,27 | (cld) |

TABLE 3b

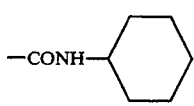

| R | Base/ solvent | excess Base (eq.) | Temp. (°C.) | Time (h) | Yield (%) | elementary analysis | | | |
|---|---|---|---|---|---|---|---|---|---|
| —CONH—⬡ | NaOH EtOH/H$_2$O 4:1 | 4 | 40 | 24 | 96 | C 60,57<br>C 60,48 | H 10,50<br>H 10,58 | N 23,55<br>N 23,50 | (cld) |

TABLE 3b-continued $$\begin{array}{c} H \\ | \\ N \\ H-N \qquad N-R \\ N \\ | \\ H \end{array}$$

| R | Base/solvent | excess Base (eq.) | Temp. (°C.) | Time (h) | Yield (%) | elementary analysis | | | | |
|---|---|---|---|---|---|---|---|---|---|---|
| —CONH—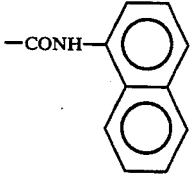 | NaOH EtOH/H$_2$O 8:1 | 4 | 40 | 24 | 97 | C 66,88<br>C 66,78 | H 7,97<br>H 7,93 | N 20,51<br>N 20,54 | | (cld) |
| —CSNH—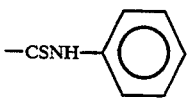 | NaOH EtOH/H$_2$O 8:1 | 4 | 40 | 24 | 95 | C 58,60<br>C 58,63 | H 8,20<br>H 8,29 | N 22,78<br>N 22,71 | S 10,43<br>S 10,37 | (cld) |
| —CSNH—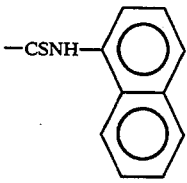 | NaOH EtOH/H$_2$O 8:1 | 4 | 40 | 24 | 96 | C 63,83<br>C 63,78 | H 7,61<br>H 7,55 | N 19,59<br>N 19,61 | S 8,97<br>S 8,91 | (cld) |

Reactions with a Compound of General Formula VI:

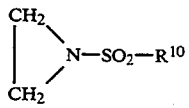

Example 12 a) Mixture of 1- and 4-formamido-10-[2-(p-tolylsulfonylamino)-ethyl]-1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to 0° C. A solution of 25.19 g (127.71 mmol) of p-tolylsulfonyl aziridine in 100 ml of toluene is instilled under a nitrogen atmosphere and then stirred for 8 hours at 80° C. It is evaporated to dryness in a vacuum and the residue is taken up in a mixture of 180 ml of ethanol/30 ml of water. Then, it is stirred for 30 minutes at room temperature. Then, it is evaporated to dryness. The residue is chromatographed on silica gel (mobile solvent=methyl-tert-butyl ester/methanol/conc. aqu. ammonia=6/2/1).

Yield: 40.61 g (88% of theory) of a vitreous solid
Analysis (relative to the anhydrous substance): Cld: C, 54.38; H, 7.86; N, 17.62; S, 8.06. Fnd: C, 54.31; H, 7.93; N, 17.58; S, 7.99.

b) 10-[2-(p-Tolylsulfonylamino)-ethyl]-1,4,7,10-tetraazacyclododecane 20.12 g (503 mmol) of sodium hydroxide is added to 40.0 g (100.62 mmol) of title compound 9a in 180 ml of ethanol/30 ml of water and refluxed for 12 hours. It is evaporated to dryness and the residue is taken up in 100 ml of water. The pH of the solution is brought to pH 10 by adding 6N hydrochloric acid. Then, it is extracted twice with 250 ml of hot toluene (80° C.). The organic phase is dried on magnesium sulfate and concentrated by evaporation in a vacuum.

Yield: 36.07 g (97% of theory) of a yellowish, vitreous solid
Analysis (relative to the anhydrous substance): Cld: C, 55.26; H, 8.46; N, 18.95; S, 8.68. Fnd: C, 55.21; H, 8.52; N, 18.90; S, 8.59.

c) Mixture of 1- and 4-formamido-10-[a-(methylsulfonylamino)-ethyl]-1,4,7,10-tetraazacyclododecane Analogously to example 12a, methylsulfonyl aziridine can be used instead of p-tolylsulfonyl aziridine.
Yield: 89% of theory
Analysis (relative to the anhydrous substance): Cld: C, 44.84; H, 8.47; N, 21.79; S, 9.97. Fnd: C, 44.76; H, 8.53; N, 21.73; S, 9.90.

d) 10-[2-(methylsulfonylamino)-ethyl]-1,4,7,10-tetraazacyclododecane

Analogously to example 12b, the title compound of example 12c can be used instead of title compound 12a.
Yield: 96% of theory
Analysis (relative to the anhydrous substance): Cld: C, 45.03; H, 9.27; N, 23.87; S, 10.93. Fnd: C, 44.96; H, 9.34; N, 23.98; S, 10.85.

Reactions with Compounds of General Formula VII:

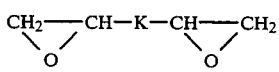

Example 13 a) Mixture of the bis-formamides of 1,1'-(2,6-dihydroxy-4-oxa-1,7-heptyl)-bis-[1,4,7,10-tetraazacyclododecane 15.9 g (133.5 mmol) of dimethylformamide-dimethylacetal (under nitrogen) is added to 20.0 g (116.1 mmol) of 1,4,7,10-tetraazacyclododecane in 200 ml of absolute toluene. It is refluxed slowly and the solvent is distilled off in this way. Then, it is concentrated by evaporation under reduced pressure. The residue is cooled to 40° C. 7.25 g (55.7 mmol) of bis-[2,3-epoxypropyl]-ether is instilled under a nitrogen atmosphere and heated slowly to 120° C. It is stirred for 24 hours at this temperature. It is cooled to room temperature and a mixture of 200 ml of methanol/100 ml of water is added. Then, it is stirred for one hour at room temperature. It is evaporated to dryness and the residue is chromatographed on silica gel (mobile solvent=methanol/isopropanol/conc. aqu. ammonia=8/2/1).

Yield: 18.63 g (63% of theory) of a vitreous solid

Analysis (relative to the anhydrous substance): Cld: C, 54.32; H, 9.50; N, 21.11. Fnd: C, 54.25; H, 9.57; N, 21.18.

b) 1,1'-(2,6-Dihydroxy-4-oxa-1,7-heptyl)-bis-(1,4,7,10-tetraazacyclododecane)

28.55 g (508.7 mmol) of potassium hydroxide is added to 18.0 g (33.92 mmol) of the title compound of example 13a in 200 ml of methanol/100 ml of water and refluxed for 2 hours. It is evaporated to dryness in a vacuum and the residue is extracted 3 times with 200 ml of hot toluene (80° C.). The organic phase is dried on potassium hydroxide and concentrated by evaporation in a vacuum.

Yield: 15.62 g (97% of theory) of a pale yellow, viscous oil, which solidifies with standing.

Analysis (relative to the anhydrous substance): Cld: C, 55.67; H, 10.62; N, 23.61. Fnd: C, 55.61; H, 10.68; N, 23.56.

For example, the compounds listed in the following table are produced analogously.

TABLE 4a

| R | Temp. (°C.) time (h) | Solvent | Equivalent diepoxide | Yield (relative to diepoxide) | elementary analysis | | | |
|---|---|---|---|---|---|---|---|---|
| ~~~O~O~~~ with OH, OH | 120° C. 24 h | — | 0,49 | 67 | C 54,33 C 54,28 | H 9,47 H 9,51 | N 19,50 N 19,38 | (cld) |
| ~~O~~O~~ with OH, OH | 120° C. 24 h | — | 0,49 | 61 | C 55,08 C 55,13 | H 9,59 H 9,50 | N 19,03 N 18,96 | (cld) |
| ~~O~~~O~~ with OH, OH | 120° C. 24 h | — | 0,49 | 60 | C 55,79 C 55,71 | H 9,70 H 9,77 | N 18,59 N 18,61 | (cld) |
| CH₂φ, O, with OH OH | 120° C. 12 h | — | 0,45 | 59 | C 59,38 C 59,31 | H 8,97 H 9,05 | N 18,47 N 18,38 | (cld) |
| C(CH₃)₂ with O O, OH OH | 130° C. 12 h | — | 0,45 | 58 | C 55,27 C 55,21 | H 9,28 H 9,37 | N 19,10 N 19,02 | (cld) |
| ~O-C₆H₄-O~ with OH, OH | 130° C. 24 h | CH₂Cl₂ | 0,49 | 61 | C 57,86 C 57,79 | H 8,74 H 8,69 | N 17,99 N 18,04 | (cld) |

TABLE 4b $$\text{H-N} \underset{\underset{H}{|}}{\overset{\overset{H}{|}}{\underset{N}{\bigg\langle}}}\bigg\rangle \text{N-R-N} \underset{\underset{H}{|}}{\overset{\overset{H}{|}}{\underset{N}{\bigg\langle}}}\bigg\rangle \text{N-H}$$

| R | Base/solvent | excess Base (eq.) | Temp. (°C.) | Time (h) | Yield (%) | elementary analysis | | | |
|---|---|---|---|---|---|---|---|---|---|
| [structure with OH, O, OH] | KOH MeOH/H₂O 2:1 | 15 | reflux | 24 | 97 | C 55,57 C 55,50 | H 10,49 H 10,58 | N 21,60 N 21,54 | (cld) |
| [structure with OH, O, O, OH] | KOH MeOH/H₂O 2:1 | 15 | reflux | 48 | 96 | C 56,36 C 56,31 | H 10,59 H 10,50 | N 21,03 N 21,11 | (cld) |
| [structure with OH, O, O, OH] | KOH MeOH/H₂O 2:1 | 15 | reflux | 48 | 98 | C 57,11 C 57,04 | H 10,69 H 10,75 | N 20,49 N 20,44 | (cld) |
| [structure with φ, O, OH, OH] | KOH EtOH/H₂O 3:1 | 15 | reflux | 24 | 97 | C 61,06 C 61,01 | H 9,88 H 9,95 | N 20,34 N 20,27 | (cld) |
| [structure with O, O, OH, OH] | KOH EtOH/H₂O 3:1 | 15 | reflux | 48 | 96 | C 56,58 C 56,53 | H 10,25 H 10,33 | N 21,11 N 21,06 | (cld) |
| [structure with OH, O-phenyl-O, OH] | KOH EtOH/H₂O 3:1 | 15 | reflux | 48 | 98 | C 59,34 C 59,28 | H 9,60 H 9,71 | N 19,77 N 19,70 | (cld) |

Example 14

Gadolinium complex of 10-(1-hydroxymethyl-2,3-dihydroxypropyl)-1,4,7-tris(carboxymethyl)-1,4,7,10-tetraazacyclododecane a) 20 l (150.55 mol) of dimethylformamide-dimethylacetal is added (under nitrogen) to 20 kg (116.10 mol) of cyclene (1,4,7,10-tetraazacyclododecane) in 140 l of toluene. It is slowly heated up and the azeotrope is distilled off from methanol/dimethylamine/toluene. Then, the solvent is completely distilled off by applying a vacuum. The remaining oil is allowed to cool to 50° C. and then 18.7 kg (about 95%) (123.22 mol) of 4,4-dimethyl-3,5,8-trioxabicyclo-(5.1.0)-octane is instilled (under nitrogen). Then, it is stirred for 24 hours at 120° C. It is cooled to room temperature and a mixture of 100 l of water/150 l of methanol is instilled. Then, it is stirred for 1 hour at 50° C. and 13.93 kg (348.3 mol) of sodium hydroxide is added. Then, it is refluxed for 8 hours. The solution is substantially evaporated to dryness, 200 l of water is added and again about 100 l of water is distilled off. Again, 100 l of water is added and this solution is extracted once with 200 l of n-butanol and then with 50 l of n-butanol. The combined butanol phases are evaporated to dryness in a vacuum and the residue is taken up in 300 l of water. Then, it is extracted twice with 50 l of ethyl acetate each. The water phase is separated and concentrated by evaporation to a volume of about 200 l.

b) 43.84 kg (464.4 mol) of chloroacetic acid is dissolved in 150 l of water and adjusted to pH 7 with 50% aqueous sodium hydroxide solution. The water phase concentrated by evaporation to a volume of about 200 l is added to this solution and heated to 80° C. The pH is kept between pH 9.5–10 by adding 50% aqueous sodium hydroxide solution. After 10 hours, another 10.96 kg (116.1 mol) of chloroacetic acid (previously neutralized as described above in 35 l of water with 50% aqueous sodium hydroxide solution) is added. It is stirred for 12 hours at 80° C. and the pH is kept between 9.5 and 10. It is allowed to cool to room temperature and adjusted with concentrated hydrochloric acid to pH 0.8. Then, it is stirred for 2 hours at 60° C. The solution is substantially evaporated to dryness in a vacuum. The residue is mixed twice with a mixture of 200 l of methanol/200 l of ethanol and evaporated to dryness. Then, the residue is absorptively precipitated for 1 hour at 50° C. with 400 l of methanol. It is filtered off from the precipitated sodium chloride, rewashed twice with 100 l of methanol and the combined filtrates are evaporated to dryness in a vacuum. The residue is dissolved in 200 l of water and added to an ion exchange column, filled with AMB 252c. It is washed with ample water and the product is eluted with a 10% aqueous ammonia solution. The product-containing fractions are substantially evaporated to dryness in a vacuum.

c) The residue is dissolved in 200 l of water and 16.31 kg (45 mol) of gadolinium oxide is added. It is refluxed for 3 hours. Then, 2 l of glacial acetic acid is added and refluxed for another 2 hours. 5 kg of activated carbon is added and stirred for 1 hour at 90° C. The solution is filtered and the filtrate is added several times on an ion exchange column cascade (consisting of IRA 67 ($OH^-$ form)) AMB 252c ($H^+$ form) (under HPLC control). The eluate is concentrated by evaporation to a volume of 300 l and stirred for 3 hours with 2 l of acid ion exchanger IR 120 ($H^+$) as well as basic exchanger IRA 67 ($OH^-$) each. It is filtered off from the exchanger and rewashed twice with 10 l of water. 5 kg of activated carbon is added to the filtrate and stirred for 2 hours at 80° C. The solution is filtered and the filtrate is concentrated by evaporation in a vacuum. The residue is recrystallized from 95% aqueous ethanol (about 400 l). The precipitate is suctioned off, rewashed twice with 80 l of pure ethanol and dried for 48 hours at 70° C. in a drying oven.

Yield: 47.6 kg (65.0% of theory) (corrected for water/relative to cyclene) of colorless crystalline powder Water content: 4.1%

Elementary analysis (relative to the anhydrous substance): Cld: C, 35.75; H, 5.17; N, 9.27; Gd, 26.00. Fnd: C, 35.92; H, 5.24; N, 9.20; Gd, 25.83.

Example 15

Dysprosium complex of 10-(1-hydroxymethyl-2,3-dihydroxypropyl)-1,4,7-tris(carboxymethyl)-1,4,7,10-tetraazacyclododecane Analogously, the corresponding dysprosium complex can be produced if, instead of gadolinium oxide, correspondingly 16.78 kg (45 mol) of dysprosium oxide is reacted.

Yield: 46.36 kg (62.7% of theory) (corrected for water/relative to cyclene)

Water content: 3.9%

Elementary analysis (relative to the anhydrous substance): Cld: C, 35.44; H, 5.12; N, 9.19; Dy, 26.64. Fnd: C, 35.35; H, 5.21; N, 9.11; Dy, 26.57.

Example 16

Gadolinium complex of 10-(2-hydroxypropyl)-1,4,7-tris(carboxymethyl)-1,4,7,10-tetraazacyclododecane a) 20 l (150.55 mol) of dimethylformamide dimethyl acetal is added (under nitrogen) to 20 kg (116.10 mol) of cyclene (1,4,7,10-tetraazacyclododecane) in 140 l of toluene. It is slowly heated up and the azeotrope is distilled off from methanol/dimethylamine/toluene. Then, the solvent is completely distilled off by applying a vacuum. The remaining oil is allowed to cool to 50° C. and then 10.11 kg (174.15 mol) of propylene oxide is instilled (under nitrogen). Then, it is refluxed for 24 hours and then excess propylene oxide is distilled off in a vacuum. It is cooled to room temperature and a mixture of 100 l of water/150 l of methanol is instilled. Then, it is stirred for 1 hour at 50° C. and 13.93 kg (348.3 mol) of sodium hydroxide is added. Then, it is refluxed for 8 hours. The solution is substantially evaporated to dryness, 200 l of water is added and again about 100 l of water is distilled off. 100 l of water is again added, and this solution is extracted once with 200 l of n-butanol and then with 100 l of n-butanol. The combined butanol phases are evaporated to dryness in a vacuum and the residue is taken up in 300 l of water. Then, it is extracted twice with 50 l of ethyl acetate each. The water phase is separated and concentrated by evaporation to a volume of about 200 l.

b) 43.84 kg (464.4 mol) of chloroacetic acid is dissolved in 150 l of water and adjusted to pH 7 with 50% aqueous sodium hydroxide solution. The water phase concentrated by evaporation to a volume of about 200 l is added to this solution and heated to 80° C. The pH is kept between pH 9.5-10 by adding 50% aqueous sodium hydroxide solution. After 10 hours, another 10.96 kg (116.1 mol) of chloroacetic acid (previously neutralized as described above in 35 l of water with 50% aqueous sodium hydroxide solution) is added. It is stirred for 12 hours at 80° C. and the pH is kept between 9.5 and 10. It is allowed to cool to room temperature and adjusted with concentrated hydrochloric acid to pH 0.8. The solution is substantially evaporated to dryness in a vacuum. The residue is mixed twice with a mixture of 200 l of methanol/200 l of ethanol and evaporated to dryness. Then, the residue is absorptively precipitated for 1 hour at 50° C. with 400 l of methanol. It is filtered off from the precipitated sodium chloride, rewashed twice with 100 l of methanol and the combined filtrates are evaporated to dryness in a vacuum. The residue is dissolved in 200 l of water and added to an ion exchange column, filled with AMB 252c. It is washed with ample water and the product is eluted with a 10% aqueous ammonia solution. The product-containing fractions are substantially evaporated to dryness in a vacuum.

c) The residue is dissolved in 200 l of water and 17.62 kg (48.6 mol) of gadolinium oxide is added. It is refluxed for 3 hours. Then, 2 l of glacial acetic acid is added and refluxed for another 2 hours. 5 kg of activated carbon is added and stirred for 1 hour at 90° C. The solution is filtered and the filtrate is added several times by an ion exchange column cascade (consisting of IRA 67 ($OH^-$ form)) of AMB 252c ($H^+$ form) (under HPLC control). The eluate is concentrated by evaporation to a volume of 300 l and stirred for 3 hours with 2 l of acid ion exchanger IR 120 ($H^+$) as well as basic exchanger IRA 67 ($OH^-$) each. It is filtered off from the exchanger and rewashed twice with 10 l of water. 5 kg of activated carbon is added to the filtrate and stirred for 2 hours at 80° C. The solution is filtered and the filtrate is concentrated by evaporation in a vacuum. The residue is recrystallized from ethanol (about 300 l). The precipitate is suctioned off, rewashed once with 50 l of pure ethanol and dried for 48 hours at 70° C. in a drying oven.

Yield: 45.22 kg (67.2% of theory) (corrected for water/relative to cyclene) of colorless crystalline powder Water content: 3.5%

Elementary analysis (relative to the anhydrous substance): Cld: C, 36.55; H, 5.23; N, 10.03; Gd, 28.15. Fnd: C, 36,68; H, 5,31; N, 9.91; Gd, 28.03.

Example 17

Dysprosium complex of 10-(2-hydroxypropyl)-1,4,7-tris(carboxymethyl)-1,4,7,10-tetraazacyclododecane Analogous to example 16c), the corresponding dysprosium complex can be produced, if, instead of gadolinium oxide, correspondingly 18.13 kg (48.6 mol) of dysprosium oxide is reacted.

Yield: 47.14 kg (65.3% of theory) (corrected for water/relative to cyclene)

Water content: 4.1%

Elementary analysis (relative to the anhydrous substance): Cld: C, 36.20; H, 5.18; N, 9.94; Dy, 28.82. Fnd: C, 36.51; H, 5,83; N, 9.39; Dy, 26.57.

Example 18

Gadolinium complex of 10-(2-hydroxy-3-methoxypropyl)-1,4,7-tris(carboxymethyl)-1,4,7,10-tetraazacyclododecane Analogously, 2,3-epoxypropylmethylether can be used instead of propylene oxide as described in Example 16. Thus, for example, 216.7 g (61% of theory) of the title compound is obtained from 100 g (0.58 mol) of 1,4,7,10-tetraazacyclododecane as colorless powder (crystallization from aqueous acetone).

Water content: 3.8%

Elementary analysis (relative to the anhydrous substance): Cld: C, 36.72; H, 5.72; N, 9.52; Gd, 26.71. Fnd: C, 36.51; H, 5.83; N, 9.39; Gd, 26.57.

Example 19

Gadolinium complex of 10-(2-hydroxy-3-benzyloxypropyl)-1,4,7-tris(carboxymethyl)-1,4,7,10-tetraazacyclododecane Analogously, 2,3-epoxypropyl-benzylether can be used instead of propylene oxide as described in Example 16. 1.1 equivalents of epoxide is used relative to 1,4,7,10-tetraazacyclododecane. It is heated for 16 hours at 110° C. (instead of 24 hours as described in Example 16). Thus 249.2 g (62% of theory) of the title compound is obtained from 100 g (0.58 mol) of 1,4,7,10-tetraazacyclododecane (crystallization from isopropanol).

Water content: 4.2%

Elementary analysis (relative to the anhydrous substance): Cld: C, 43.36; H, 5.31; N, 8.43; Gd, 23.65. Fnd: C, 43,21; H, 5.40; N, 8.32; Gd, 23.48.

Example 20

Gadolinium complex of 10-(2,3,4-trihydroxybutyl)-1,4,7-tris(carboxymethyl)-1,4,7,10-tetraazacyclododecane Analogously, 2-(2,2-dimethyl-1,3-dioxolan-4-yl)-ethylene oxide can be employed instead of 4,4-dimethyl-3,5,8-trioxabicyclo-(5.1.0)-octane as described in Example 14, with 1.1 equivalents of epoxide being used relative to 1,4,7,10-tetraazacyclododecane. It is heated for 16 hours at 110° C. (instead of 24 hours as described in Example 14). Thus 232.8 g (64% of theory) of the title compound is obtained as colorless, crystalline powder from 100 g (0.58 mol) of 1,4,7,10-tetraazacyclododecane (crystallization from 90% aqueous ethanol).

Water content: 3.5%

Elementary analysis (relative to the anhydrous substance): Cld: C, 35.75; H, 5.17; N, 9.26; Gd, 26.00. Fnd: C, 35.55; H, 5.23; N, 9.14; Gd, 25.87.

Example 21

Gadolinium complex of 10-(2-hydroxy-3-tert.-butoxy-propyl)-1,4,7-tris(carboxymethyl)-1,4,7,10-tetraazacyclododecane Analogously, 2,3-epoxypropyl-tert.-butyl ester can be used instead of propylene oxide as described in Example 16. 1.1 equivalents of epoxide is used relative to 1,4,7,10-tetraazacyclododecane. It is heated for 16 hours at 110° C. (instead of 24 hours as described in Example 16). Thus 225 g (59% of theory) of the title compound is obtained as colorless, crystalline powder from 100 g (0.58 mol) of 1,4,7,10-tetraazacyclododecane (crystallization from acetone/ethanol).

Water content: 4.0%

Elementary analysis (relative to the anhydrous substance): Cld: C, 39.99; H, 5.91; N, 8.88; Gd, 24.93. Fnd: C, 39.81; H, 6.05; N, 8.73; Gd, 24.82.

Example 22

Gadolinium complex of 10-(2,6,7-trihydroxy-4-oxaheptyl)-1,4,7-tris(carboxymethyl)-1,4,7,10-tetraazacyclododecane Analogously, 2,2-dimethyl-4-(2',3'-epoxy)-propoxymethyl-1,3-dioxolane can be used instead of 4,4-dimethyl-3,5,8-trioxabicyclo-(5.1.0)-octane as described in Example 14. 1.1 equivalents of epoxide is used relative to 1,4,7,10-tetraazacyclododecane. It is heated for 16 hours at 110° C. (instead of 24 hours as described in Example 14). Thus 242.2 g (62% of theory) of the title compound is obtained as colorless, crystalline powder from 100 g (0.58 mol) of 1,4,7,10-tetraazacyclododecane (crystallization from ethanol).

Water content: 3.6%

Elementary analysis (relative to the anhydrous substance): Cld: C, 37.03; H, 5.44; N; 8.64; Gd, 24.24. Fnd: C, 36.91; H, 5.58; N, 8.49; Gd, 24.13.

Example 23

Gadolinium complex of 10-(2-hydroxy-3-isopropoxypropyl)-1,4,7-tris(carboxymethyl)-1,4,7,10-tetraazacyclododecane Analogously, 2,3-epoxypropylisopropyl ether can be used instead of propylene oxide as described in Example 16. 1.1 equivalents of epoxide is used relative to 1,4,7,10-tetraazacyclododecane. It is heated for 16 hours at 110° C. (instead of 24 hours as described in Example 16). Thus 232.5 g (63% of theory) of the title compound is obtained as colorless, crystalline powder from 100 g (0.58 mol) of 1,4,7,10-tetraazacyclododecane (crystallization from isopropanol).

Water content: 3.1%

Elementary analysis (relative to the anhydrous substance): Cld: C, 38.95; H, 5.72; N, 9.08; Gd, 25.50. Fnd: C, 38.85; H, 5.81; N, 8.93; Gd, 25.35.

Example 24

Gadolinium complex of 10-(2-hydroxy-2-methylpropyl)-1,4,7-tris(carboxymethyl)-1,4,7,10-tetraazacyclododecane Analogously, iso-butylene oxide can be used instead of propylene oxide as described in Example 16. Thus for example 209.4 g (60% of theory) of the title compound is obtained as colorless powder from 100 g (0.58 mol) of 1,4,7,10-tetraazacyclododecane (crystallization from aqueous acetone).

Water content: 4.0%

Elementary analysis (relative to the anhydrous substance): Cld: C, 37.75; H, 5.46; N, 9.78; Gd, 27.46. Fnd: C, 37.61; H, 5.53; N, 9.70; Gd, 27.38.

Example 25

Gadolinium complex of 10-(2-hydroxy-3-phenoxypropyl)-1,4,7-tris(carboxymethyl)-1,4,7,10-tetraazacyclododecane Analogously, 2,3-epoxypropyl-phenyl ether can be used instead of propylene oxide as described in Example 16. 1.1 equivalents of epoxide is used relative to 1,4,7,10-tetraazacyclododecane. It is heated for 16 hours at 110° C. (instead of 24 hours as described in Example 16).

Thus 252.4 g (64% of theory) of the title compound is obtained as colorless, crystalline powder from 100 g (0.58 mol) of 1,4,7,10-tetraazacyclododecane (crystallization from aqueous acetone).

Water content: 3.7%

Elementary analysis (relative to the anhydrous substance): Cld: C, 43.49; H, 5.02; N, 8.45; Gd, 23.73. Fnd: C, 43.31; H, 5.11; N, 8.38; Gd, 23.65.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for production of mono-N-substituted tetraazacyclododecane and tetraazacyclotetradecane compounds of formula I

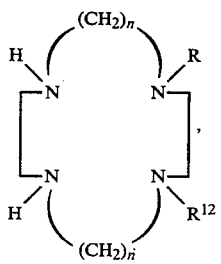

(I')

wherein n is 2 or 3; and

R is β-carboxylalkyl, β-carboxylate alkyl, β-cyanide alkyl, β-carboxamidoalkyl, β-hydroxyalkyl, aminocarbonyl, aminothiocarbonyl, β-sulfamoylalkyl or a second tetraazacyclododecane or tetraazacyclotetradecane molecule bound by a bis(β-hydroxy)-alkylene chain, wherein carboxyl and hydroxy groups present are optionally in protected form, comprising:

reacting a compound of formula II, wherein n is 2 or 3, obtained from 1,4,7,10-tetraazacyclododecane or 1,4,8,11-tetraazacyclotetradecane,

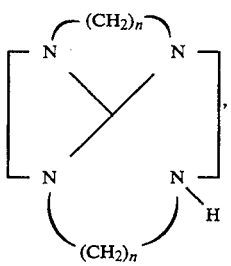

(II)

with an α,β-unsaturated ester, an α,β-unsaturated amide, an α,β-unsaturated nitrile, an epoxide, an isocyanate, an isothiocyanate, an aziridine or a bisepoxide, with or without solvent, at 0°–220° C., within 1–48 hours and optionally, at a pressure of up to 100 atm.;

the resultant reaction mixture, after cooling to −20° C.–80° C. is mixed with a mixture of water/organic solvent and stirred for 0.5 to 12 hours at −20° C.–25° C.;

the resultant, optionally isolated, intermediate products having a formyl group on a nitrogen atom are reacted by adding an inorganic base or an acid at 0°–150° C. within 1–72 hours, with stirring; and optionally removing protecting groups and isolating the end product of formula I.

2. A process according to claim 1, wherein R is a

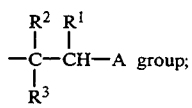

$R^1$ is H, straight-chain $C_1$–$C_6$-alkyl, cyclic $C_1$–$C_6$-alkyl, phenyl, or benzyl, wherein phenyl or benzyl can be optionally substituted by 1 to 2 Cl, Br, nitro, $C_1$–$C_7$-alkoxy, $C_7$–$C_{10}$-aralkoxy, and/or $CO_2R^4$ groups;

$R^2$ and $R^3$, independent of one another, are each H, straight-chain $C_1$–$C_6$-alkyl, cyclic $C_1$–$C_6$-alkyl, $CO_2R^4$, phenyl, or benzyl, wherein phenyl or benzyl can be optionally substituted by 1 to 2 Cl, Br, nitro, $C_1$–$C_7$-alkoxy, $C_7$–$C_{10}$-aralkoxy, and/or $CO_2R^4$ groups;

$R^4$ is H, $C_1$–$C_6$-alkyl, phenyl or benzyl;

A is CN, $CO_2R^4$ or

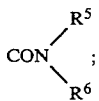

$R^5$ and $R^6$, independent of one another, are each H; a saturated or unsaturated, straight-chain, branched-chain or cyclic hydrocarbon radical with up to 16 C atoms, said hydrocarbon radical being optionally interrupted by 1 to 8 oxygen atoms, 1 to 3 phenylene groups, and/or 1 to 3 phenylenoxy groups, and being optionally substituted by 1 to 5 hydroxy groups and/or 1 to 2 $CO_2R^4$ radicals; phenyl optionally substituted by 1 to 3 hydroxy or $C_1$–$C_6$ alkoxy groups; benzyl optionally substituted by 1 to 3 hydroxy or $C_1$–$C_6$-alkoxy groups; or $R^5$ and $R^6$, together with the nitrogen atom, are a saturated or unsaturated 5- or 6-ring, optionally containing another nitrogen, oxygen, sulfur atom or a carbonyl group, and which optionally is substituted by 1 to 3 $C_1$–$C_6$ alkyl radicals optionally substituted by 1 to 3 hydroxy radicals;

wherein hydroxy and/or carboxyl groups, if present are optionally protected; and said compound of formula II is reacted with an α,β-unsaturated ester, α,β-unsaturated amide, or α,β-unsaturated nitrile of formula III

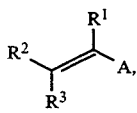

(III)

in which $R^1$, $R^2$, $R^3$ and A have the above-indicated meanings, optionally present hydroxy and/or carboxyl groups being optionally protected.

3. A process according to claim 1, wherein R is a

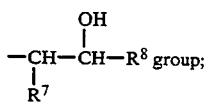

group;

$R^7$ and $R^8$, independent of one another, are each H, $C_1$-$C_{20}$-alkyl optionally interrupted by 1 to 10 oxygen atoms, a phenylene group, a phenylenoxy group or a phenylenedioxy group, and which is optionally substituted by 1 to 3 $C_1$-$C_6$-alkyl, 1 to 3 trifluoromethyl, 1 to 7 hydroxy, 1 to 3 $C_1$-$C_7$-alkoxy, 1 to 3 $C_7$-$C_{10}$ aralkoxy, 1 to 2 $CO_2R^4$ and/or 1 to 2 phenoxy or phenyl groups optionally substituted by 1 to 2 Cl, Br, nitro or $C_1$-$C_6$ alkoxy radicals, wherein optionally present hydroxy radicals are optionally in protected form; and said compound of formula II is reacted with an epoxide of formula IV

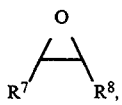 (IV)

wherein $R^7$ and $R^8$ have the above-indicated meanings, optionally present hydroxy and/or carboxyl groups being optionally protected.

4. A process according to claim 1, wherein R is

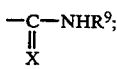

X is oxygen or sulfur;
$R^9$ is phenyl, 1- or 2-naphthyl, straight-chain $C_1$-$C_6$-alkyl or cyclic $C_1$-$C_6$-alkyl; and
said compound of formula II is reacted with an isocyanate or thioisocyanate of formula V $$R^9-N=C=X \quad (V),$$

in which X and $R^9$ have the above-indicated meanings, with or without solvent, at 0° C. to 180° C.

5. A process according to claim 1, wherein
R is —$(CH_2)_2$—NH—$SO_2$—$R^{10}$;
$R^{10}$ is $C_1$-$C_6$-alkyl, —$CF_3$, or phenyl optionally substituted by a $C_1$-$C_6$-alkyl, Cl, Br, or nitro; and
said compound of formula II is reacted with an aziridine of formula VI

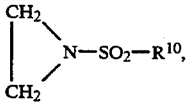 (VI)

in which $R^{10}$ has the above-indicated meaning, with solvent, at 0° C. to 180° C.

6. A process according to claim 1, wherein
R is a 1,4,7,10-tetraazacyclododecane or 1,4,7,10-tetraazacyclotetradecane molecule bound by a bis(β-hydroxy)-alkylene chain of the formula

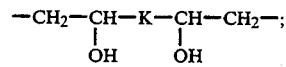

K is a $C_0$-$C_{16}$-alkylene chain optionally substituted by 1 to 6 hydroxy, 1 to 6 $C_1$-$C_7$-hydroxyalkyl, 1 to 8 $C_1$-$C_7$-alkoxy, 1 to 8 $C_7$-$C_{10}$-aralkoxy and/or 1 to 2 benzyloxy groups, and is optionally interrupted by 1 to 6 oxygen atoms, 1 to 2 phenylene, phenylenoxy or phenylenedioxy groups, optionally present hydroxy groups being optionally in protected form; and said compound of formula II is reacted with a bisepoxide of formula VII

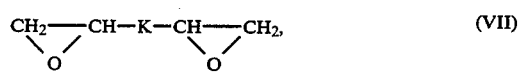 (VII)

in which K has the above-indicated meaning, optionally present hydroxy groups being optionally protected.

7. A process according to claim 1, wherein said process is performed from the 1,4,7,10-tetraazacyclododecane or 1,4,8,11-tetraazacyclotetradecane starting material, without isolation of intermediate products, to said compound of formula I.

8. In a process for production of a metal complex of N-substituted-tri-N-carboxyalkyl tetraaza macrocycle wherein a mono-N-substituted tetraazacyclododecane or mono-N-substituted tetraazacyclotetradecane compound is prepared as an intermediate, the improvement wherein said intermediate is prepared according to the process of claim 1.

9. In a process for production of a N-substituted-tri-N-carboxyalkyl tetraaza macrocycle complexing agent wherein a mono-N-substituted tetraazacyclododecane or mono-N-substituted tetraazacyclotetradecane compound is prepared as an intermediate, the improvement wherein said intermediate is prepared according to the process of claim 1.

10. A process for production of a N-substituted-tri-N-carboxyalkyl-1,4,7,10-tetraazacyclododecane or a N-substituted-tri-N-carboxyalkyl-1,4,8,11-tetraazacyclotetradecane compound comprising:

preparing a compound of formula I according to claim 1;

reacting said compound of formula I, in the presence of a base, with a compound of formula X, $$X-CH_2-COOZ \quad (X),$$

wherein
X is a leaving group, and
Z is hydrogen, a carboxy protective group or a metal cation,
optionally after protection of hydroxy or carboxy groups optionally present in said compound of formula I, in a polar solvent at −10° C.-170° C. within 1-100 hours; and
optionally removing protecting groups.

11. A process for production of a metal complex of N-β-hydroxyalkyl-tri-N-carboxyalkyl-1,4,7,10-tetraazacyclododecane or N-β-hydroxyalkyl-tri-N-carboxyalkyl-1,4,8,11-tetraazacyclotetradecane compound of formula VIII

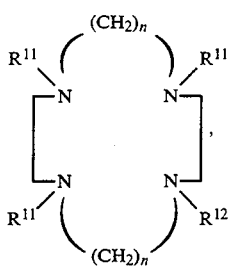

(VIII)

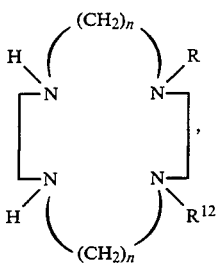

(I')

wherein $R^{11}$ is —$CH_2$—COOY;

Y is hydrogen or a metal ion equivalent of an element of atomic numbers 21-32, 37-39, 42-51 or 57-83, provided that at least two substituents Y stand for metal equivalents;

n is 2 or 3;

$R^{12}$ is

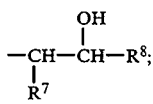

$R^7$ and $R^8$, independent of one another, are each hydrogen, $C_1$-$C_{20}$ alkyl optionally interrupted by 1 to 10 oxygen atoms, a phenylene, phenylenoxy or phenylenedioxy group, and optionally substituted by 1 to 3 $C_1$-$C_6$ alkyl, 1 to 3 -trifluoromethyl, 1 to 7 hydroxy, 1 to 3 $C_1$-$C_7$ alkoxy, 1 to 3 $C_7$-$C_{10}$ aralkoxy, 1 to 2 $CO_2R^{4'}$ radicals, and/or 1 to 2 phenoxy or phenyl groups optionally substituted by 1 to 2 chloro, bromo, nitro or $C_1$-$C_6$ alkoxy radicals;

$R^{4'}$ is hydrogen, $C_1$-$C_6$ alkyl, $C_6$-$C_{10}$ aryl or $C_6$-$C_{10}$-Ar($C_1$-$C_4$)alkyl;

wherein optionally present hydroxy radicals being optionally present in protected form; and salts thereof with inorganic and/or organic bases, amino acids or amino acid amides;

said process comprising reacting, according to claim 3, a compound of formula II with a compound of formula IV to obtain an intermediate of formula IX

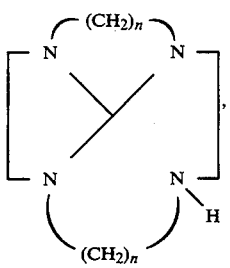

(II)

wherein $R^{12}$ the above-indicated meaning, optionally present hydro, groups and/or carboxy groups are optionally protected;

said intermediate of formula IX is saponified to form an intermediate of formula I', said intermediate of formula I' is reacted, in the presence of a base, with a compound of formula X, $$X—CH_2—COOZ \quad (X),$$

wherein

X is a leaving group, and

Z is hydrogen, a carboxy protective group or a metal cation, optionally after protection of hydroxy or carboxy groups optionally present in said intermediate of formula (I'), in a polar solvent at $-10°$ C.$-170°$ C. within 1-100 hours;

protecting groups are then optionally cleaved off and the resultant complexing agent of formula XI,

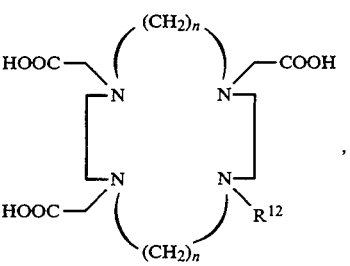

(XI)

is reacted with a metal oxide or metal salt of an element of atomic numbers 21-32, 37-39, 42-51 or 57-83; and optionally, hydrogen atoms of acid groups are replaced by cations of inorganic or organic bases, amino acids or amino acid amides, or acid groups are optionally converted, completely or partially, into esters or amides.

12. A process according to claim 11, wherein the reaction to form a compound of formula IX is performed at a temperature of 20° C.-120° C., without solvent or in an aprotic solvent.

13. A process according to claim 11, wherein the reaction to form a compound of general formula I' is performed at a temperature of 20° C.-210° C. in aqueous alcohols with addition of sodium hydroxide, potassium hydroxide or hydrochloric acid.

14. A process according to claim 11, wherein said compound of formula X is chloroacetic acid.

15. A process according to claim 11, wherein the reaction to form a compound of formula XI is performed, without protection of hydroxy or carboxy groups, at a temperature of 40° C.-100° C. in water within 3-24 hours.

16. A process according to claim 11, wherein $R^7$ and $R^8$, independent of one another, are each hydrogen, $C_1$-$C_{10}$ alkyl optionally interrupted by 1 to 5 oxygen atoms, a phenylene, phenylenoxy or phenylenedioxy group, and which is optionally substituted by 1 to 3 $C_1$–$C_6$ alkyl, 1 to 3 trifluoromethyl, 1 to 5 hydroxy, 1 to 3 $C_1$–$C_7$alkoxy, 1 to 2 $CO_2R^{4'}$, and/or 1 to 2 phenoxy or phenyl groups optionally substituted by a nitro group or a $C_1$–$C_6$ alkoxy, and $R^{4'}$ is hydrogen, $C_1$–$C_6$ alkyl or benzyl.

17. A process according to claim 11, wherein a metal complex of 10-(1-hydroxymethyl-2,3-dihydroxypropyl)-1,4,7-tris(carboxymethyl)-1,4,7,10-tetraazacyclododecane is produced.

18. A process according to claim 11, wherein a metal complex of 10-(2-hydroxypropyl)-1,4,7-tris(carboxymethyl)-1,4,7,10-tetraazacyclododecane is produced.

19. A process according to claim 17, wherein a gadolinium or dysprosium complex of 10-(1-hydroxymethyl-2,3-dihydroxypropyl)-1,4,7-tris(carboxymethyl)-1,4,7,10-tetraazacyclododecane is produced.

20. A process according to claim 18, wherein a gadolinium or dysprosium complex of 10-(2-hydroxypropyl)-1,4,7-tris(carboxymethyl)-1,4,7,10-tetraazacyclododecaneis produced.

* * * * *

UNITED STATES PATENT AND TRADEMARK OFFICE
CERTIFICATE OF CORRECTION

PATENT NO. : 5,410,043
DATED : April 25, 1995
INVENTOR(S) : Johannes PLATZEK et al.

It is certified that error appears in the above-indentified patent and that said Letters Patent is hereby corrected as shown below:

Claim 1; column 43, lines 23-35: Change

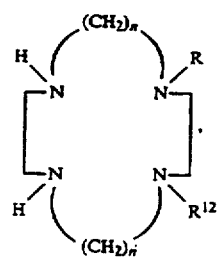 (I')

to

UNITED STATES PATENT AND TRADEMARK OFFICE
CERTIFICATE OF CORRECTION

PATENT NO. : 5,410,043
DATED : April 25, 1995
INVENTOR(S) : Johannes Platzek et al.

It is certified that error appears in the above-indentified patent and that said Letters Patent is hereby corrected as shown below:

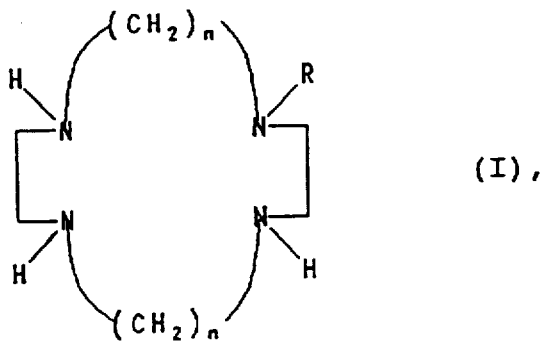

(I),

Signed and Sealed this

Fifth Day of December, 1995

Attest:

*Attesting Officer*

BRUCE LEHMAN

*Commissioner of Patents and Trademarks*